United States Patent
Dowd

(10) Patent No.: US 10,167,520 B2
(45) Date of Patent: Jan. 1, 2019

(54) UNIVERSAL OR BROAD RANGE ASSAYS AND MULTI-TAG SAMPLE SPECIFIC DIAGNOSTIC PROCESS USING NON-OPTICAL SEQUENCING

(71) Applicant: Scot E. Dowd, Shallowater, TX (US)

(72) Inventor: Scot E. Dowd, Shallowater, TX (US)

( * ) Notice: Subject to any disclaimer, the term of this patent is extended or adjusted under 35 U.S.C. 154(b) by 0 days.

(21) Appl. No.: 13/707,295

(22) Filed: Dec. 6, 2012

(65) Prior Publication Data
US 2013/0157874 A1 Jun. 20, 2013

Related U.S. Application Data

(60) Provisional application No. 61/567,540, filed on Dec. 6, 2011, provisional application No. 61/591,589, filed on Jan. 27, 2012.

(51) Int. Cl.
| | | |
|---|---|---|
| *C12Q 1/68* | (2018.01) | |
| *C12P 19/34* | (2006.01) | |
| *C12Q 1/689* | (2018.01) | |
| *C12Q 1/6895* | (2018.01) | |
| *C12Q 1/70* | (2006.01) | |

(52) U.S. Cl.
CPC ........... *C12Q 1/689* (2013.01); *C12Q 1/6895* (2013.01); *C12Q 1/70* (2013.01); *C12Q 1/701* (2013.01); *C12Q 2600/16* (2013.01)

(58) Field of Classification Search
USPC ......................................................... 435/6.1
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 5,089,386 A | 2/1992 | Stackebrandt et al. | |
| 5,162,199 A | 11/1992 | Stern et al. | |
| 5,389,513 A | 2/1995 | Baquero et al. | |
| 5,437,978 A | 8/1995 | Ubukata et al. | |
| 5,708,169 A | 1/1998 | Hester, Jr. et al. | |
| 5,763,167 A | 6/1998 | Conrad | |
| 6,001,564 A | 12/1999 | Bergeron et al. | |
| 6,268,132 B1 | 7/2001 | Conrad | |
| 7,501,251 B2 | 3/2009 | Koster et al. | |
| 7,948,015 B2 | 5/2011 | Rothberg et al. | |
| 2003/0228571 A1* | 12/2003 | Ecker .................. | C12Q 1/6816 435/5 |
| 2007/0031875 A1* | 2/2007 | Buzby ............................... | 435/6 |
| 2009/0311677 A1* | 12/2009 | Reeves .................. | C12Q 1/689 435/6.16 |
| 2010/0035239 A1* | 2/2010 | Sampath et al. ................. | 435/6 |
| 2010/0035252 A1* | 2/2010 | Rothberg et al. ................ | 435/6 |

FOREIGN PATENT DOCUMENTS

| | | | |
|---|---|---|---|
| WO | WO9820157 | 5/1998 | |
| WO | WO 2011011094 A1 * | 1/2011 | ........... C12Q 1/6809 |

OTHER PUBLICATIONS

Burja et al. Applied microbiology and biotechnology 72.6 (2006): 1161-1169.*
Janse et al. Appl. Environ. Microbiol. 2004, 70(7):3979-3987.*
Lowe et al. Nucleic Acids Research, vol. 18, No. 7, p. 1757-1761,1990.*
Blast analysis of SEQ ID No. 83 and 84.*
Fu et al., "Sequencing exons 5 to 8 of the p53 gene by MALDI-TOF mass spectrometry," Nature Biotechnology, 1998, vol. 16, pp. 381-384.*
Ross et al., "Quantitative Approach to Single-Nucleotide Polymorphism Analysis Using MALDI-TOF Mass Spectrometery," BioTechniques, 2000, vol. 29, No. 3, pp. 620-629.*
Oros-Sichler et al., "A new semi-nested PCR protocol to amplify large 18S rRnA gene fragments for PCR-DDGE analysis of soil fungal communities," Journal of Microbiological Methods, 2006, vol. 65, pp. 63-75.*
Miflin et al "Development of a 23S rRNA-based PCR assay for the identification of Pasteurella multocida," Letters in Applied Microbiology, 2001, vol. 33, pp. 216-221.*
Chakravorty et al., "A detailed analysis of 16S ribosomal RNA gene segments for the diagnosis of pathogenic bacteria," Journal of Microbiological Methods, 2007, vol. 69, pp. 330-339.*
Boreman et al., "PCR Primers That Amplify Fungal rRNA Genes from Environmental Samples," Applied and Environmental Microbiology, 2000, vol. 66, No. 10, pp. 4356-4360.*
Ding et al., "A high-throughput gene expression analysis technique using competitive PCR and matrix-assisted laser desorption ionization time-of-flight MS," PNAS, 2003, vol. 100, No. 6, pp. 3059-3064.*
Dowd et al., "Evaluation of the bacterial diversity in the feces of cattle using 16S rDNA bacterial tag-encoded FLX amplicon pyrosequencing (bTEFAP)," BMC Microbiology, 2008, vol. 8, No. 125, pp. 1-8.*
Aebersold, R., et al, "Mass spectrometry-based proteomics," Nature 2003, 422(6928):198-207.
Ansorge, W. J., "Next-generation DNA sequencing techniques," New Biotechnology, 2009, 25(4):195-203.
Ewing, B., et al, "Base-calling of automated sequencer traces using Phred.?I. Accuracy?Assessment," Genome Research 1998, 8(3):175-185.

(Continued)

*Primary Examiner* — Young J Kim
(74) *Attorney, Agent, or Firm* — Edwin S. Flores; Chalker Flores, LLP

(57) ABSTRACT

The present invention includes a method for determining the identify of an organism or virus in a sample comprising the steps of: isolating DNA or RNA from the sample; combining the DNA or RNA directly or with one or more universal or target specific amplification primers, wherein the one or more primers are specific for one or more group of target microorganisms or virus; and amplifying the DNA, or the RNA following reverse transcription with a reverse transcriptase; and contacting the amplification product with one or more species-, organism- or virus-specific detectable marker.

26 Claims, 1 Drawing Sheet

Specification includes a Sequence Listing.

(56) References Cited

OTHER PUBLICATIONS

Hammond, P.A., et al, "Encapsulation of a liquid-sensing microchip using SU-8 photoresist," Microelectronic Engineering 73-74, 2004, pp. 893-897.
Lutz, et al, "Recognition of a Non-Standard base Pair by Thermostable DNA Polymerases," Bioorganic & Medicinal Chemistry Letters, 8: 1149-1152 (1998).
Martineau, F., et al, "Species-specific and ubiquitous-DNA-based assays for rapid identification of *Staphylococcus aureus*," Journal of Clinical Microbiology, 1998, 36(3):618-623.
Metzker, M. L., "Sequencing technologies—the next generation," Nature Reviews Genetics, 2009, 11(1):31-46.
Milgrew, M.J., et al, "A large transistor-based sensor array chip for direct extracellular imaging," Sensors and Actuators, 2005, B:111-112, pp. 347-353.
Milgrew, M.J., et al, "Matching the Transconductance Characteristics of CMOS ISFET Arrays by Removing Trapped Charge," IEEE Transactions on Electron Devices, vol. 55, No. 4, Apr. 2008.
Ohtsuki, et al, "Unnatural Base Pairs for Specific Transcription," Proc. Natl. Acad. Sci., 98: 4922-4925 (2001).
Pourmand, N., et al, "Direct electrical detection of DNA synthesis," Proceedings of the National Academy of Sciences, 2006, 103(17):6466-6470.
Purushothaman, S., et al, "Protons and single nucleotide polymorphism detection: A simple use for the Ion Sensitive Field Effect Transistor," Sensors and Actuators, 2006, B:114, pp. 964-968.
Reeve, J., "Archaebacteria then . . . Archaes now (are there really no archaeal pathogens?)," Journal of Bacteriology, 1999, 181(12):3613-3617.
Ronaghi, M, "Pyrosequencing sheds light on DNA sequencing," Genome Research, 2001, 11(1):3-11.
Rothberg, J.M., et al, "An integrated semiconductor device enabling non-optical genome sequencing," Nature, 2011, 475(7356):348-352.

Schuster, S. C., "Next-generation sequencing transforms today's biology," Nature, 2008, 5(1), 16-18.
Seela, F., et al, "Fluorescent DNA: the development of 7-deazapurine nucleoside triphosphates applicable for sequencing at the single molecule level," Journal of Biotechnology, 2001, vol. 86, pp. 269-279.
Theuwissen, A., "CMOS image sensors: State-of-the-art," Solid-State Electronics, 2008, 52(9):1401-1406.
Van Burik, J., et al, "Panfungal PCR Assay for Detection of Fungal Infection in Human Blood Specimens," Journal of Clinical Microbiology, 1998, 36(5):1169.
Virta, P., et al, "Fluorescent 7- and 8-Methyl Etheno Derivatives of Adenosine and 6-Amino-9-ethylpurine: Syntheses and Fluorescence Properties," Nucleosides, Nucleotides and Nucleic Acids, 2003, 22:1, pp. 85-89.
International Search Report for PCT/US2012/068260 dated Mar. 20, 2013.
Written Opinion of the International Searching Authority for PCT/US2012/068260 dated Mar. 20, 2013.
Hamady, M., et al, "Error-correcting barcoded primers for pyrosequencing hundreds of samples in multiplex," Nature Methods, 2008, vol. 5, No. 3, pp. 235-237.
Moorthie, S., "Review of massively parallel DNA sequencing technologies," The HUGO Journal, 2011, vol. 5, pp. 1-12.
Rothberg, J.M., et al, "An integrated semiconductor device enabling non-optical genome sequencing," Nature, 2011, vol. 475, pp. 348-552.
Junemann, S., et al., "Bacterial Community Shift in Treated Periodontitis Patients Revealed by Ion Torrent 16S rRNA Gene Amplicon Sequencing," www.plosone.org, Aug. 2012, vol. 7:8, e41606, 8 pp.
Prajapati, J., et al., "Genomic Analysis of Dairy Starter Culture *Streptococcus thermophilus* MTCC 5461," J. Microbiol. Biotechnol., vol. 23:4, Jan. 24, 2013, pp. 459-466.
Yergeau, E., et al., "Next-Generation Sequencing of Microbial Communities in the Athabasca River and its Tributaries in Relation to Oil Sands Mining Activities," Applied and Environmental Microbiology, vol. 78, No. 21, Nov. 2012, pp. 7626-7637.

* cited by examiner

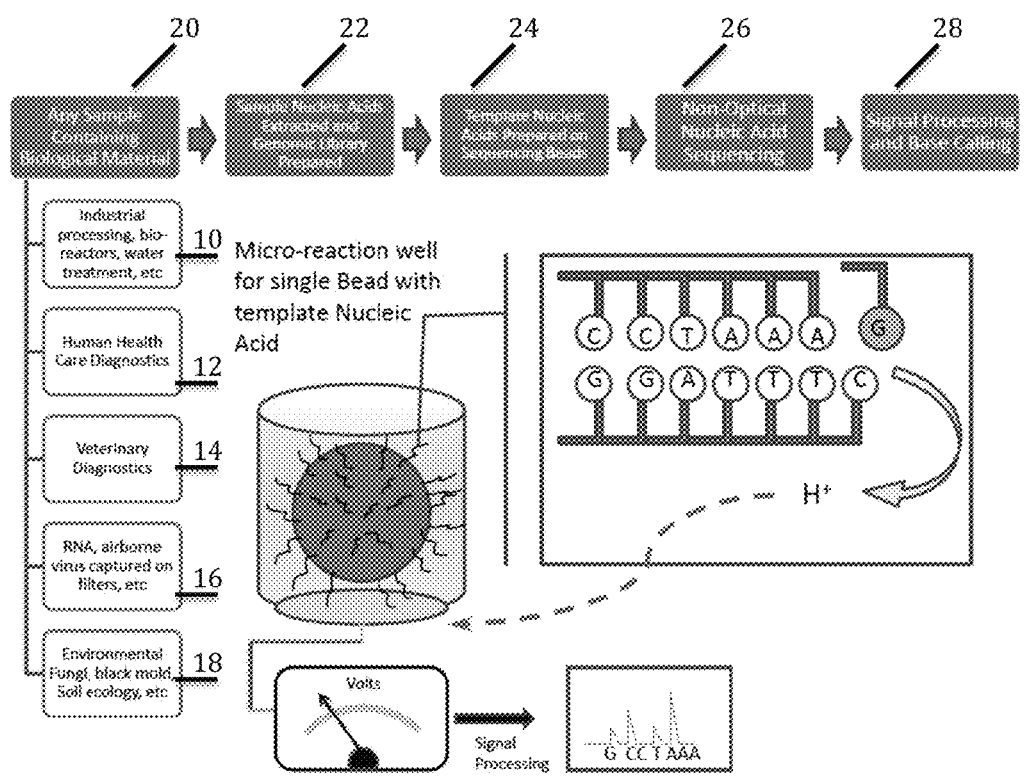

SEQUENCE LISTING

<160> NUMBER OF SEQ ID NOS: 285

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gactgcgtac caattc                                                       16

```
<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatgagtcct gagtaa                                                       16

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (11)..(11)
<223> OTHER INFORMATION: a, c, t, g, unknown or other

<400> SEQUENCE: 3
gagtttgatc ntggctcag                                                    19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agrgtttgat cmtggctcag                                                   20

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other

<400> SEQUENCE: 5
gtnttacngc ggckgctg                                                     18

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtttgatcct ggctcag                                                      17

<210> SEQ ID NO 7
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gwattaccgc ggckgctg                                                    18

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agagtttgat ymtggctcag                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agagtttgat cctggcttag                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agggttcgat tctggctcag                                                  20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agaatttgat cttggttcag                                                  20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agrgtttgat cmtggctcag                                                  20

<210> SEQ ID NO 13
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 13
ggggtttcta ctggtggt                                                    18

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccctckgsa aagccttctt c                                                21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
staatggtct ggcttagacg                                                  20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcggccatcc atctgtatgt                                                  20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other

<400> SEQUENCE: 17
ggngactggg acttctgg                                                    18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: a, c, t, g, unknown or other

<400> SEQUENCE: 18
```

-continued cgsaagaaga gncgsaag                    18

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccattyctgc aacgmggcc                    19

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggggtttcta ctggtggt                    18

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cccctckgsa aagccttctt c                 21

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccatctcatc cctgcgtgtc tccgactcag         30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cctatcccct gtgtgccttg gcagtctcag         30

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
staatggtct ggcttagacg                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcggccatcc atctgtatgt                                                    20

<210> SEQ ID NO 26
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgcccgcgcc gccccgcgcc cgtcccgccg ccccccgcccg cctacgggag gcagcag         57

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccgtcaattc mtttragttt                                                    20

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cctacgggag gcagcag                                                       17

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccgtcaattc mtttragttt                                                    20

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccattyctgc aacgmggcc                                                    19

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other

<400> SEQUENCE: 32
ggngactggg acttctgg                                                     18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: a, c, t, g, unknown or other

<400> SEQUENCE: 33
cgsaagaaga gncgsaag                                                     18

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cggacgggtg agtaacgcgt ga                                                22

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggcgvacggg tgagtaa                                                      17

```
<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other

<400> SEQUENCE: 36
ccgcngcngc tggcac                                                    16

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cctacgggag gcagcag                                                   17

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccgtcaattc mtttragt                                                  18

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
arcgaacgct ggcggca                                                   17

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tacgaattty acctctaca                                                 19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 41 ggggaattttt ggacaatggg                                          20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acgcatttca ctgctacacg                                           20

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cmatgccgcg tgtgtgaa                                             18

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
actccccagg cggtcdactt a                                         21

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccggawtyat tgggtttaaa ggg                                       23

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggtaaggttc ctcgcgta                                             18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggaattttcc gcaatggg                                                    18

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gactacwggg gtatctaatc c                                                21

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggctgcagtc gagratct                                                    18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgtgtgagcc cccgtcaa                                                    18

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggcagcagtr gggaatcttc                                                  20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
acacytagya ctcatcgttt                                                  20

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 53
gagtttgaty htggctcag                                                19

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
acgghtacct tgttacgact t                                             21

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agagtttgat cctggctcag                                               20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
agagtttgat cmtggctcag                                               20

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cggacgggtg agtaacgcgt ga                                            22

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccagactcct acgggaggca gc                                            22

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
```
ctcctacggg aggcagcag                                                19

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggggaatytt ccgcaatggg                                               20

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtgccagcmg ccgcggtaa                                                19

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gtgccagcag ccgcggtaa                                                19

<210> SEQ ID NO 63
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
crcctgggga gtrcrg                                                   16

<210> SEQ ID NO 64
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
caacgagcgc aaccct                                                   16

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65

```
gggctacaca cgygcwac                                                 18
```

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66

```
gwattaccgc ggckgctg                                                 18
```

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

```
gactacwggg gtatctaatc ccwtt                                         25
```

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

```
cttgtgcggg cccccgtcaa ttc                                           23
```

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: Inosine

<400> SEQUENCE: 69

```
gtcaattcnt ttgagtttya ryc                                           23
```

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(13)
<223> OTHER INFORMATION: Inosine

<400> SEQUENCE: 70

```
ccccgtcaat tcntttgagt ttyar                                         25
```

<210> SEQ ID NO 71
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 71
ccgtcaattc mtttragttt                                               20

<210> SEQ ID NO 72
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
agggttgcgc tcgttg                                                   16

<210> SEQ ID NO 73
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gayttgacgt catccm                                                   16

<210> SEQ ID NO 74
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gayttgacgt catcca                                                   16

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cggtgtgtac aagrccygrg a                                             21

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cgggcggtgt gtacaagrcc ygrga                                         25

<210> SEQ ID NO 77
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 77
gacgggcggt gtgtrca                                                    17

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ggttaccttg ttacgactt                                                  19

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ctcctacggg aggcagcag                                                  19

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ttgtgcgggc cccgtcaat t                                                21

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccgtcaattc mtttragttt                                                 20

<210> SEQ ID NO 82
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cctacgggag gcagcag                                                    17

<210> SEQ ID NO 83
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 83
gtgccagcmg ccgcggtaa                                                19

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggactacvsg ggtatctaat                                               20

<210> SEQ ID NO 85
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: a, c, t, g, unknown or other

<400> SEQUENCE: 85
gtgccagcmg cngcgg                                                   16

<210> SEQ ID NO 86
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 86
gggttncgnt cgttr                                                    15

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
accmggatta gataccckg                                                19

<210> SEQ ID NO 88
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 88
acgggcggtg tgtrc                                                  15

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aaactyaaak gaattgacgg                                             20

<210> SEQ ID NO 90
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acgggcggtg tgtrc                                                  15

<210> SEQ ID NO 91
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ttgacggggg cccgcac                                                17

<210> SEQ ID NO 92
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
taccttgtta cgactt                                                 16

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
yaacgagcgc aaccc                                                  15

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 94
gggttacctt gttacgactt                                                    20

<210> SEQ ID NO 95
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
aaggaggtga tccagcc                                                       17

<210> SEQ ID NO 96
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gcaacgagcg caaccc                                                        16

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
agattgccca ggcctctcg                                                     19

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ccatcgtagt cttaaccata aac                                                23

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tggcctatct tgttggtctg t                                                  21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
```

-continued gaatcaaacct gacaaggcaa c                      21

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
aagattagcc tgcgtccgat                         20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gtcaacttat cgcgtttgct                         20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
tcysgcatcg atgaagaacg                         20

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gatatgctta agttcagcgg g                       21

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tggagggcaa gtctggtg                           18

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tcggcatagt ttatggttaa g       21

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
aaggtctccg taggtgaac       19

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gtatccctac ctgatccgag       20

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
tccgtaggtg aacctgcgg       19

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tcctccgctt attgatatgc       20

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
tccgtaggtg aacctgcgg       19

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tcctccgctt attgatatgc       20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tcctaccctt tgtgaatttg                                          20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ctgcgttctt catcgttgcg                                          20

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cttggtcatt tagaggaagt aa                                       22

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tcctccgctt attgatatgc                                          20

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
aacctggttg atcctgccag t                                        21

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gctattggag ctggaattac                                          20

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
ccgcggtaat tccagctc                                                      18

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
cgttatcgga attaaccaga c                                                  21

<210> SEQ ID NO 121
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
gtacacaccg cccgtc                                                        16

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
tgatccttct gcaggttcac ctac                                               24

<210> SEQ ID NO 123
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
ggagggcaag tctggt                                                        16

<210> SEQ ID NO 124
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
cggccatgca ccacc                                                         15

-continued

```
<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ccctaygggg ygcascag                                                  18

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gagargwrgt gcatggcc                                                  18

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gtgctccccc gccaattcct                                                20

<210> SEQ ID NO 128
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gygcascagk cgmgaaw                                                   17

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ggactacvsg ggtatctaat                                                20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
acggggygca gcaggcgcga                                                20

<210> SEQ ID NO 131
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gtgctccccc gccaattcct                                              20

<210> SEQ ID NO 132
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cccgggtatc taatcc                                                  16

<210> SEQ ID NO 133
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
tgggaaactg ggaaactggg tctaata                                      27

<210> SEQ ID NO 134
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cccgcacgcc caagttaagc tgtgag                                       26

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gcggcaccaa ctggggctgg t                                            21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
catgaabggc tcccartcca t                                            21

<210> SEQ ID NO 137
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ttggagggca agtctggtgc c                                              21

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gaacccaaac actttggttt cc                                             22

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t, g, unknown or other

<400> SEQUENCE: 139
tayatgtcng gyggtgthgg                                                20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 140
acrttcatng crtagttngg                                                20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cgytgttcmt cgacagccag                                                20

<210> SEQ ID NO 142
<211> LENGTH: 20
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 142
cgsaccttst tgccrtygcg                                                    20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
staatggtct ggcttagacg                                                    20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
gcggccatcc atctgtatgt                                                    20

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ggggtttcta ctggtggt                                                      18

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cccctckgsa aagccttctt c                                                  21

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
staatggtct ggcttagacg                                                    20

<210> SEQ ID NO 148
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 148
gcggccatcc atctgtatgt                                                 20

<210> SEQ ID NO 149
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cgcccgcgcc gccccgcgcc cgtcccgccg ccccccgcccg cctacgggag gcagcag       57

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ccgtcaattc mtttragttt                                                 20

<210> SEQ ID NO 151
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
cctacgggag gcagcag                                                    17

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ccgtcaattc mtttragttt                                                 20

<210> SEQ ID NO 153
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other

<400> SEQUENCE: 153
ggngactggg acttctgg                                                   18

<210> SEQ ID NO 154
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
ccattyctgc aacgmggcc                                                  19

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other

<400> SEQUENCE: 155
ggngactggg acttctgg                                                   18

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: a, c, t, g, unknown or other

<400> SEQUENCE: 156
cgsaagaaga gncgsaag                                                   18

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
ggggtttcta ctggtggt                                                   18

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
cccctckgsa aagccttctt c                                               21

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 159
staatggtct ggcttagacg                                                    20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
gcggccatcc atctgtatgt                                                    20

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other

<400> SEQUENCE: 161
ggngactggg acttctgg                                                      18

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: a, c, t, g, unknown or other

<400> SEQUENCE: 162
cgsaagaaga gncgsaag                                                      18

<210> SEQ ID NO 163
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ccattyctgc aacgmggcc                                                     19

<210> SEQ ID NO 164
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ggggaccagc tcatggtgg                                                     19

<210> SEQ ID NO 165

<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
aatgcaaaaa gaacagtaaa ca				22

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
gtgaacgtca aggaaacggg				20

<210> SEQ ID NO 167
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 167
gaattcggat gcgtcttga				19

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 168
gtcggwttca cmcagtacgc				20

<210> SEQ ID NO 169
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 169
tgccctcgtc kgactggta				19

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 170
caacatcgty catacmcagg g				21

<210> SEQ ID NO 171
<211> LENGTH: 17

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gtgtagcagt taccgca                                                  17

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
ccggataggm tggkbccrta                                               20

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gtgcacaasg crtadrcctt cah                                           23

<210> SEQ ID NO 174
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ggmatggtkc cstggca                                                  17

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
gcctcgatca grttrtgg                                                 18

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: a, c, t, g, unknown or other

<400> SEQUENCE: 176
gntaccttgt tacgactt                                                 18
```

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
cttaatttga ctcaacacgg                                                    20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 178
tcacanttng gatantccca                                                    20

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 179
actcanntna atntnaaata ngc                                                23

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 180
agctaggyct aacattgtta                                          20

<210> SEQ ID NO 181
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
tccgttgttg aaagtgatc                                           19

<210> SEQ ID NO 182
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gatcggcgat cggtgagt                                            18

<210> SEQ ID NO 183
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
tgagactctc ggatcgg                                             17

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
actgaccctc aagcakgtg                                           19

<210> SEQ ID NO 185
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tgctaaatag ccaggctgy                                           19

<210> SEQ ID NO 186
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 186
cttggtcatt tagaggaagt aa                                               22

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ttgatatgct taagttcagc g                                                21

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
cgcggcctat catcagcttg ttg                                              23

<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
ccgtactccc caggcgggg                                                   19

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ggcccagatc gtttaccgtg aa                                               22

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
tctcacaagc tgctagggag tca                                              23

<210> SEQ ID NO 192
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
agggttcgat tccggag            17

<210> SEQ ID NO 193
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
gctgctggca ccagact            17

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
aacggctacc acatctaagg aacc            24

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
ttaaatacga atgcccccaa ctgt            24

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(9)
<223> OTHER INFORMATION: a, c, t, g, unknown or other

<400> SEQUENCE: 196
gtgtttcnnt gcgtgagcct gttt            24

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other

<400> SEQUENCE: 197
gtggtaancc gcacacacca aant            24

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
aatcggcaca gtttgatgag ctg                                           23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
cgtggagcgt gcggtttaat ttg                                           23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ctgctgctgc tgctactact gta                                           23

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
tccagacgtc ttatgccttg cac                                           23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tccttcattg ttgttgagcc gag                                           23

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
caacatcgcc acgtgtagca ca                                            22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
aggtcgttga agaacgacgt ga                                           22

<210> SEQ ID NO 205
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
tggcaaagac cattgtgtgc aa                                           22

<210> SEQ ID NO 206
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
aattgtggca gcggcagatg ta                                           22

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
tagttcacca tctttcgggt cg                                           22

<210> SEQ ID NO 208
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
accatggttg tgacggataa cg                                           22

<210> SEQ ID NO 209
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tggcaaatgc tttcgcagta gg                                           22

<210> SEQ ID NO 210
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
atggccgttc ttagttggtg ga                                              22

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tgtgtacaaa gggcagggac g                                               21

<210> SEQ ID NO 212
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tgtctaagtg cggctgtcat ag                                              22

<210> SEQ ID NO 213
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tagtgctgct caccaccatc ct                                              22

<210> SEQ ID NO 214
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
tggagcctgc ggcttaattt ga                                              22

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
tgtgtacaaa gggcagggac g                                               21

<210> SEQ ID NO 216

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
tgatgccctt agatgttctg gg                                              22

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tgtgtacaaa gggcagggac g                                               21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
aaaggaattg acggaagggc a                                               21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
agcccaagat gtctaagggc a                                               21

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
tagtggtgca tggccgttct ta                                              22

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tgtgtacaaa gggcagggac g                                               21

<210> SEQ ID NO 222
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
acgcaaagtt ggcgacgact a                                             21

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
cggcttaaac gaacttgtgc a                                             21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
atggtattgg cttaccgtgg c                                             21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
caccagactt gccctccaat t                                             21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ttgtcggtcg ccagcagata c                                             21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
cggtgaacgg cgggatgaac t                                             21

<210> SEQ ID NO 228
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 228
gcatatcaat aagcggagga aa                                              22

<210> SEQ ID NO 229
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
ggtccgtgtt tcaagacgg                                                  19

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
actcccatga aaccatgcta cg                                              22

<210> SEQ ID NO 231
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
acatactttg acattcgcgg cg                                              22

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
ataccgccaa gtgggaagca g                                               21

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
tccgtagcat ggtttcatgg ga                                              22

<210> SEQ ID NO 234
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 234
tcctgtgagt gggaacaaac cg                                              22

<210> SEQ ID NO 235
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tctcagtgga acgaagctga tg                                              22

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
ttgccggtcg ttcaaagagg ta                                              22

<210> SEQ ID NO 237
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
cacccatgtt gccagtgctg tt                                              22

<210> SEQ ID NO 238
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
catgctgcgc aacgatacca at                                              22

<210> SEQ ID NO 239
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
tggcatcgag gatgaactgc ct                                              22

<210> SEQ ID NO 240
<211> LENGTH: 22
<212> TYPE: DNA
<213> ORGANISM: Artificial Sequence
<220> FEATURE:
```

<223> OTHER INFORMATION: Description of Artificial Sequence: Synthetic
       primer

<400> SEQUENCE: 240
tcatcaacca cctgcctgct ca                                              22

<210> SEQ ID NO 241
<211> LENGTH: 22
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 241
cattgcggtg gtggttgaat gg                                              22

<210> SEQ ID NO 242
<211> LENGTH: 22
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 242
taagggttga cggagccagc at                                              22

<210> SEQ ID NO 243
<211> LENGTH: 22
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 243
agccctggta gccaatgttg ta                                              22

<210> SEQ ID NO 244
<211> LENGTH: 22
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 244
tgcactatca cctctcggtg ct                                              22

<210> SEQ ID NO 245
<211> LENGTH: 22
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 245
agaaatgggt cctgaatctg gg                                              22

<210> SEQ ID NO 246
<211> LENGTH: 22
<212> TYPE: DNA
<213> ORGANISM: Artificial Sequence
<220> FEATURE:
<223> OTHER INFORMATION: Description of Artificial Sequence: Synthetic

```
                                  primer

<400> SEQUENCE: 246
aaaccgccgt tggtaacacc at                                              22

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
agcagtgtag atgatcgtgc ag                                              22

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 248
accacaggng tngagaagcc t                                               21

<210> SEQ ID NO 249
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 249
tgcagccatg gatgacttnc an                                              22

<210> SEQ ID NO 250
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
tgagaaagct tgccctcaat gc                                              22

<210> SEQ ID NO 251
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 251
acactttccc natngagcct tc                                            22

<210> SEQ ID NO 252
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
ggaaggaatg attgcaggtt gg                                            22

<210> SEQ ID NO 253
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ggtctggttg cacttgtgtt tgg                                           23

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
tcagttatgc tccttgccca ctg                                           23

<210> SEQ ID NO 255
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
tccttgccca ctgtgaatga gac                                           23

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
```
tcctatttgc aggttggagt gcc                                          23

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
tcctatttgc aggttggagt gcc                                          23

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
aatctgcaac acaactgggt gtc                                          23

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
acaatgctcc ctgtgggatt gag                                          23

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
agcatctgcg gagaatgtga agg                                          23

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
atactgggag catgtccaac acc                                          23

<210> SEQ ID NO 262
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
aagctgtgat tctgtggttg ctg                                          23

<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
tggcccattg ccctgttgta ttt                                              23

<210> SEQ ID NO 264
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 264
taymgntayg yngaytgg                                                    18

<210> SEQ ID NO 265
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 265
atnggrtana cnccccca                                                    17

<210> SEQ ID NO 266
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
aaaggyggwa tcggyaartc caccac                                           26

<210> SEQ ID NO 267
<211> LENGTH: 26
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 267
atgatggcsa tgtaygcsgc saacaa                                          26

<210> SEQ ID NO 268
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
tgsgcyttgt cytcrcggat bggcat                                          26

<210> SEQ ID NO 269
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
tgggcyttgt tytcrcggat yggcat                                          26

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
aacgcctaya csacsctgtt c                                               21

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: a, c, t, g, unknown or other

<400> SEQUENCE: 271
tccatgtgca gngcrtggca gaa                                             23

<210> SEQ ID NO 272

<400> SEQUENCE: 272

000

<210> SEQ ID NO 273

<400> SEQUENCE: 273

000

<210> SEQ ID NO 274
```

```
<400> SEQUENCE: 274

000

<210> SEQ ID NO 275
<400> SEQUENCE: 275

000

<210> SEQ ID NO 276
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
taygtsggsc argaraa                                                    17

<210> SEQ ID NO 277
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
ttytcrtacc abgtbgc                                                    17

<210> SEQ ID NO 278
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
ggggtttcta ctggtggt                                                   18

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
cccctckgsa aagccttctt c                                               21

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
gatgacagca tgtcagggag                                                 20
```

```
<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
gttgacaggt gtaggtccta c                                              21

<210> SEQ ID NO 282
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
gcaagcgggt gacaatggct ttat                                           24

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
gacaacgagc tttgcttcat cgca                                           24

<210> SEQ ID NO 284
<211> LENGTH: 12
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(12)
<223> OTHER INFORMATION: a, c, t, g, unknown or other

<400> SEQUENCE: 284
nnnnnnnnnn nn                                                        12

<210> SEQ ID NO 285
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(18)
<223> OTHER INFORMATION: a, c, t, g, unknown or other

<400> SEQUENCE: 285
nnnnnnnnnn nnnnnnnn                                                  18
```

UNIVERSAL OR BROAD RANGE ASSAYS AND MULTI-TAG SAMPLE SPECIFIC DIAGNOSTIC PROCESS USING NON-OPTICAL SEQUENCING

CROSS-REFERENCE TO RELATED APPLICATIONS

This application claims priority to U.S. Provisional Application Ser. No. 61/567,540, filed Dec. 6, 2011, and U.S. Provisional Application Ser. No. 61/591,589, filed Jan. 27, 2012 the entire contents of each of which is incorporated herein by reference.

TECHNICAL FIELD OF THE INVENTION

The present invention relates in general to the field of diagnosing and monitoring industrial and environmental microbial processes, medical and veterinary diagnosis and medical and veterinary treatment, and more particularly, to universal or broad range assays and multi-tag sample specific diagnostic process using non-optical sequencing.

STATEMENT OF FEDERALLY FUNDED RESEARCH

None.

INCORPORATION-BY-REFERENCE OF MATERIALS FILED ON COMPACT DISC

None.

The instant application contains a Sequence Listing which has been submitted in ASCII format via EFS-Web and is hereby incorporated by reference in its entirety. Said ASCII copy, created on Jan. 31, 2013, is named MDNA_1000 SL.txt and is 68,449 bytes in size.

BACKGROUND OF THE INVENTION

Without limiting the scope of the invention, its background is described in connection with classical methods for the identification of microorganisms.

Microorganisms are traditionally identified by their ability to utilize different substrates as a source of carbon and nitrogen through the use of biochemical tests such as the API20E™ system (bioMerieux). For susceptibility testing, clinical microbiology laboratories use methods including disk diffusion, agar dilution and broth microdilution. The detection and identification of biological agents are important in determining the best course of treatment and/or eradication of the biological agent in natural infections, and other cases; such as, but not limited to, biological warfare. Although identifications based on biochemical tests and antibacterial susceptibility tests are cost-effective, generally two days are required to obtain preliminary results due to the necessity of two successive overnight incubations to identify the bacteria from clinical specimens as well as to determine their susceptibility to antimicrobial agents.

There are commercially available automated systems that combine these biochemical identification and susceptibility testing processes; such as, the Mircroscan WalkAway system, the Sensititre ARIS (automatic reading and incubation system) and the Vitek system from bioMerieux, which use sophisticated and expensive apparatus for faster microbial identification and susceptibility testing [1]. These systems require shorter incubation periods, thereby allowing most bacterial identifications and susceptibility testing to be performed in less than 6 hours. Nevertheless, these systems typically require the primary isolation of the bacteria or fungi as a pure culture, a process that takes approximately 18 hours for a pure culture or 48 hours for a mixed culture. Thus, the time from sample reception to identification is at minimum 24 hours. Moreover, it is now accepted that approximately 90% of bacteria, and a large percentage of fungi are fastidious organisms, or do not grow in culture. Identification must rely on labor-intensive techniques such as direct microscopic examination of the specimens and by direct and/or indirect immunological assays. Cultivation of most parasites is impractical in the clinical laboratory. Hence, microscopic examination of the specimen, a few immunological tests and clinical symptoms are often the only methods used for identification; an identification that frequently remains presumptive.

Clinical Specimens Tested in Clinical Microbiology Laboratories. Most clinical specimens received in clinical microbiology laboratories are urine and blood samples. The remaining percentage of clinical specimens comprise various biological fluids including sputum, pus, cerebrospinal fluid, synovial fluid, respiratory tract aspirate, deep pus, ear aspirate, pleural and pericardial fluid, peritoneal fluid, and others. Infections of the urinary tract, the respiratory tract and the bloodstream are usually of bacterial etiology and require antimicrobial therapy. Typically all clinical samples received in a clinical microbiology laboratory are tested routinely for the identification of bacteria and antibiotic susceptibility.

Conventional Pathogen Identification from Clinical Specimens. Urine Specimens. A myriad of tests have been developed to search for pathogens in urine specimens. However, the gold standard remains the classical semi-quantitative plate culture method in which 1 µL of urine is streaked on agar plates and incubated for 18-24 hours. Colonies are then counted to determine the total number of colony forming units (CFU) per liter of urine. A bacterial urinary tract infection (UTI) is normally associated with a bacterial count of $10^7$ CFU/L or more in urine. However, infections with less than $10^7$ CFU/L in urine are possible, particularly in patients with a high incidence of diseases or those catheterized [3]. It is not uncommon for 80% of urine specimens tested in clinical microbiology laboratories are considered negative (i.e. bacterial count of less than $10^7$ CFU/L;). Urine specimens found positive by culture are further characterized using standard biochemical tests to identify the bacterial pathogen and are also tested for susceptibility to antibiotics. The biochemical and susceptibility testing normally require 18-24 hours of incubation.

Accurate and rapid urine screening methods for bacterial pathogens would allow a faster identification of negative specimens and a more efficient treatment and care management of patients. Several rapid identification methods (Uriscreen™, UTIscreen™, Flash Track™ and others) have been compared to standard biochemical methods, which are based on culture of the bacterial pathogens. Although much faster, these rapid tests showed low sensitivities and poor specificities as well as a high number of false negative and false positive results.

Blood Specimens. Blood specimens received in a clinical microbiology laboratory are also submitted for culture. Blood culture systems may be manual, semi-automated or completely automated. The Bactec™ system (from Becton Dickinson) and the Bactalert™ system (from Organon Teklika corporation) are the two most widely used automated blood culture systems. These systems incubate blood culture bottles under optimal conditions for growth of most bacteria. Bacterial growth is monitored continuously to detect early positives by using highly sensitive bacterial growth detectors. Once growth is detected, a gram stain is performed directly from the blood culture and then used to inoculate nutrient agar plates. Subsequently, bacterial identification and susceptibility testing are carried out from isolated bacterial colonies with automated systems as described previously. Blood culture bottles are normally reported as negative if no growth is detected after an incubation of 6 to 7 days. Normally, the vast majority of blood cultures are reported negative.

Other Clinical Samples. Upon receipt by the clinical microbiology laboratory, all body fluids other than blood and urine that are from normally sterile sites (i.e. cerebrospinal, synovial, pleural, pericardial and others) are processed for direct microscopic examination and subsequent culture. Again, most clinical samples are negative for culture. In all these normally sterile sites, tests for the universal detection of algae, archaea, bacteria, fungi and parasites would be very useful.

Regarding clinical specimens that are not from sterile sites such as sputum or stool specimens, the laboratory diagnosis by culture is more problematic because of the contamination by the normal flora. The bacterial or fungal pathogens potentially associated with the infection are grown and separated from the colonizing microbes using selective methods and then identified as described previously. For DNA-based assays for species or genus or family or group detection and identification as well as for the detection of antimicrobial agents' resistance genes from these specimens would be very useful and would offer several advantages over classical identification and susceptibility testing methods.

DNA-Based Assays with any specimen. There is an obvious need for rapid and accurate diagnostic tests for the detection and identification of algae, archaea, bacteria, fungi and parasites directly from clinical specimens. Common diagnostic methods involving DNA sequencing use florescence detected by a camera or laser and/or other optical method for signal detection and measurement. The process of DNA sequencing specifically refers to the determination of the nucleotide order of a particular DNA fragment. DNA-based technologies are rapid and accurate and offer a great potential to improve the diagnosis of infectious diseases [6-8]). The Universal DNA probes and amplification primers which are objects of the present invention for DNA sequencing applications using non-optical base detection methods are applicable for the detection and identification of algae, archaea, bacteria, fungi, and parasites directly from any clinical specimen such as blood, urine, sputum, cerebrospinal fluid, pus, genital and gastro-intestinal tracts, skin or any other type of specimens. These assays are also applicable for the detection and identification, or confirmation of organism identification from microbial cultures (e.g. blood cultures, bacterial or fungal colonies on nutrient agar, or liquid cell cultures in nutrient broth). The DNA based tests proposed in this invention are superior in terms of both speed and accuracy to standard biochemical methods currently used for routine diagnosis from any clinical specimens in microbiology laboratories. Since these tests can be performed in less than 48 hours, they provide the clinician with new diagnostic tools which should contribute to a better management of patients with infectious diseases. Specimens from sources other than humans (e.g. other primates, birds, plants, mammals, farm animals, livestock, food products, environment such as water or soil, and others) may also be tested with these assays.

High Percentage of Culture-Negative Specimens. Among all the clinical specimens received for routine diagnosis, approximately 80% of urine specimens and even more (around 95%) for other types of normally sterile clinical specimens are negative for the presence of bacterial pathogens. It would also be desirable, in addition to identify bacteria at the species or genus or family or group level in a given specimen, to screen out the high proportion of negative clinical specimens with a DNA-based test detecting the presence of any bacterium (i.e., universal bacterial detection). As disclosed in the present invention, such a screening test may be based on DNA amplification by PCR and sequencing of hypervariable regions near a highly conserved genetic target found universally in all bacteria. Specimens negative for bacteria would not be amplified by this assay. On the other hand, those that are positive for any bacterium would give a positive amplification signal, and could be moved forward in the processing pipeline into sequencing analysis for organism identification. Similarly, hyper variable regions of conserved genes of fungi and parasites could serve to map the organisms to its most closely related taxonomic level, and establish the presence of that specific organism in the specimen known to be pathogenic or opportunistic pathogens.

Development of Rapid DNA Sequencing Based Diagnostic Tests. A rapid diagnostic test should have a significant impact on the management of infections. DNA amplification and sequencing technologies offer several advantages over conventional methods for the identification of pathogens and antimicrobial agents resistance genes from clinical samples [6, 9]). There is no need for culture of the pathogens, hence the organisms can be detected directly from clinical samples, thereby reducing the time associated with the isolation and identification of pathogens, and reducing the amount of hazardous biological material that need be disposed. Furthermore, DNA-based sequencing assays are more accurate for microbial identification than currently used phenotypic identification systems which are based on biochemical tests and/or microscopic examination. Commercially available DNA-based sequencing technologies are currently used in clinical microbiology laboratories, mainly for the detection and identification of fastidious bacterial pathogens such as *Mycobacterium tuberculosis*, *Chlamydia trachomatis*, *Neisseria gonorrhoeae* as well as for the detection of a variety of viruses [10]. There are also other commercially available DNA-based assays that are used as culture confirmation assays. DNA sequencing based tests for the detection and identification of bacterial pathogens which are detectable by the present invention, for example: *Staphylococcus* sp. (U.S. Pat. No. 5,437,978), *Neisseria* sp. (U.S. Pat. No. 5,162,199 and European patent serial no. 0,337,896,131) and *Listeria monocytogenes* (U.S. Pat. Nos. 5,389,513 and 5,089,386). However, the diagnostic tests described in these patents are based either on rRNA genes or on genetic targets detected by optical detection based sequencing techniques, different from those described in the present invention. To our knowledge there are no other patents published by others describing the use of non-optical based sequencing technology described in the present invention for microbiological diagnostic purposes.

Although there are phenotypic identification methods which have been used for more than 125 years in clinical microbiology laboratories, these methods do not provide information fast enough to be useful in the initial management of patients. There is a need to increase the speed of the diagnosis of commonly encountered bacterial, fungal and parasitical infections. Besides being much faster, DNA-based diagnostic tests are more accurate than standard biochemical tests presently used for diagnosis because the microbial genotype (e.g. DNA level) is more stable than the phenotype (e.g. physiologic level).

Bacteria, fungi and parasites encompass numerous well-known microbial pathogens. Other microorganisms could also be pathogens or associated with human diseases. For example, achlorophylious algae of the *Prototheca* genus can infect humans. Archaea, especially methanogens, are present in the gut flora of humans [11, 12]. Methanogens have been associated to pathologic manifestations in the colon, vagina, and mouth [11, 13, 14].

In addition to the identification of the infectious agent, it is often desirable to identify harmful toxins and/or to monitor the sensitivity of the microorganism to antimicrobial agents. As presented in this methodology, genetic identification of the microorganism could be performed simultaneously with toxin and antimicrobial agents' resistance genes.

Knowledge of the genomic sequences of algal, archaeal, bacterial, fungal and parasitical species continuously increases as indicated by the number of sequences available from public databases such as GenBank. In order to determine good candidates for diagnostic purposes, one could select sequences for DNA-based assays from genomes available from public databases for (i) the species-specific detection and identification of commonly encountered bacterial, fungal and parasitical pathogens, (ii) the genus-specific detection and identification of commonly encountered bacterial, fungal or parasitical pathogens, (iii) the family-specific detection and identification of commonly encountered bacterial, fungal or parasitical pathogens, (iv) the group-specific detection and identification of commonly encountered bacterial, fungal or parasitical pathogens, (v) the universal detection of algal, archaeal, bacterial, fungal or parasitical pathogens, and/or (vi) the specific detection and identification of antimicrobial agents resistance genes, and/or (vii) the specific detection and identification of bacterial toxin genes. All of the above types of DNA-based assays may be performed directly from any type of clinical specimens or from a microbial culture.

U.S. Pat. No. 6,001,564, and patent publication WO98/20157, teach that DNA sequences described are suitable for: (i) the species-specific detection and identification of clinically important bacterial pathogens, (ii) the universal detection of bacteria, and (iii) the detection of antimicrobial agents resistance genes using amplification, hybridization, and sequencing technology dependent on optical detection systems.

Patent publication WO98/20157 describes proprietary tuf DNA sequences as well as tuf sequences selected from public databases (in both cases, fragments of at least 100 base pairs), as well as oligonucleotide probes and amplification primers derived from these sequences. All the nucleic acid sequences described in that patent publication can be used in: (a) detecting the presence of bacteria and fungi; and (b) detecting specifically at the species, genus, family or group levels, the presence of bacteria and fungi and antimicrobial agents resistance genes associated with these pathogens. However, it is noted that these methods and kits need to be improved, since the ideal kit and method should be capable of diagnosing close to 100% of microbial pathogens and associated antimicrobial agents resistance genes and toxins genes. For example, infections caused by *Enterococcus faecium* have become a clinical problem because of its resistance to many antibiotics. Both the detection of these bacteria and the evaluation of their resistance profiles are desirable. Non-optical genomic sequencing methods developed for the detection of pathogens in humans and animals fulfill this need by utilizing a non-optical sequencing platform, different than what was originally patented.

Use of highly conserved genes for identification and diagnostics. Highly conserved genes are useful for identification of microorganisms. For bacteria, the most studied genes for identification of microorganisms are the universally conserved ribosomal RNA genes (rRNA). Among those, the principal targets used for identification purposes are the small subunit (SSU) ribosomal 16S rRNA genes (in prokaryotes) and 18S rRNA genes (in eukaryotes) [15, 16]. The rRNA genes are also the most commonly used targets for universal detection of bacteria [17, 18] and fungi [19].

However, it may be difficult to discriminate between closely related species when using primers derived from the 16S rRNA. In some instances, 16S rRNA sequence identity may not be sufficient to guarantee species identity [20], and it has been shown that inter operon sequence variation as well as strain to strain variation could undermine the application of 16S rRNA for identification purposes [21]. The heat shock proteins (HSP) are another family of highly conserved proteins. These ubiquitous proteins in bacteria and eukaryotes are expressed in answer to external stress agents. One of the most described of these HSP is HSP 60. This protein is highly conserved at the amino acid level; hence it has been useful for phylogenetic studies. Similar to 16S rRNA, it would be difficult to discriminate between species using the HSP 60 nucleotide sequences as a diagnostic tool. However, Goh et al. identified a highly conserved region flanking a variable region in HSP 60, which led to the design of universal primers amplifying this variable region (Goh, et al., U.S. Pat. No. 5,708,160). The sequence variations in the resulting amplicons were found useful for the design of species-specific assays.

DNA Sequencing Techniques. In recent years, the overall understanding in biology has been dramatically advanced through the development of fast, sensitive nucleic acid sequencing methods using automated DNA sequencers. DNA sequencing technology is opening many new fields, and is finding novel applications in biology and medicine that go far beyond the initial goal of elucidating the order of nucleotide bases in a molecule of DNA. Nucleic acid sequencing refers to the process of determining the primary structure of an unbranched biopolymer, which results in a symbolic linear depiction know as a 'sequence' that summarizes much of the atomic level structure of the sequenced molecule. The process of DNA sequencing specifically refers to the determination of nucleotide order of a particular DNA fragment. It is now possible to analyze entire genomes of bacteria, fungi, viruses, animals, and plants. The major limitations to current sequencing methods are the accuracy of the sequence, the length of an individual fragment (template) that can be sequenced, the cost of the sequence analysis, and the length of time it takes to determine the sequence. Some recent efforts have made significant progress towards the development of methods that improve the ability to prepare genomes for sequencing, and to successfully sequence large numbers of templates simultaneously. The DNA sequencing technologies can be reviewed and considered in a variety of ways. However, for the purposes of this patent, we can separate the technologies fundamentally based on the type of detection method used in the technique to determine nucleotide order. These detection platforms can be separated into Optical and Non-Optical based methods of genome sequencing. Since the inception of genome sequencing in the 1970's until now, Optical genome sequencing techniques have predominated sequencing technology, and are denoted by the requirement for imaging technology, electromagnetic intermediates either in the form of X-rays.

Optical methods of genome sequencing. Maxam-Gilbert Sequencing: The first two sequencing methods were described in 1977. Maxam and Gilbert described a chemical degradation method [26], and Sanger described an enzymatic dideoxy method (also called the chain-terminator method)[22], which became the method of choice since it was perceived to be more efficient and use fewer toxic chemicals and lower amounts of radioactivity than the method of Maxam and Gilbert. Maxam and Gilbert's method requires radioactive labeling at one 5' end of the DNA, typically by a kinase reaction using gamma-32P ATP, and purification of the DNA fragment to be sequenced. The fragments are visualized by exposing the gel with the separated fragments to X-ray film, presenting a series of bands that each correspond to a labeled DNA fragment. From these fragments, the DNA sequence could be inferred.

Sanger Sequencing: The Sanger method uses dideoxynucleotide triphosphates (ddNTPs) as DNA chain terminators to generate a set of nucleic acid fragments which are different in length by one nucleotide. Each one of these chain terminating dideoxynucleotides (e.g. ddATP, ddGTP, ddCTP, and ddTTP) can be uniquely labeled. The labeled DNA fragments are size separated by gel electrophoresis with single nucleotide resolution. Variations in the electrophoretic process include applications of slab gels, capillaries, or microfluidic devices using denaturing polyacrylamide-urea gels, or other gradient poor-size polymer matrices. The DNA bands are then visualized by autoradiography or UV light, and the DNA sequence can be directly read off the X-ray film or gel image. Different variations of chain-termination sequencing have included tagging with nucleotides containing radioactive phosphorus for radiolabelling, or using a primer labeled with a fluorescent dyes. Dye-primer sequencing facilitates reading in an optical system for faster and more economical analysis and automation. Thus, these fluorescently labeled ddNTPs and primers set the stage for automated, high-throughput DNA sequencing.

Dye-terminator sequencing: Dye-terminator sequencing is differentiated by labeling the chain terminator ddNTPs each with a different and unique fluorescent dye that emits light at a unique wavelength. This permits sequencing in a single reaction, rather than four reactions as in the labeled-primer method. Even though the Sanger sequencing was the only method utilized in the parallel consortia that determined the complete human genome, many limitations of the Sanger processed were realized; such as, the need for gels or polymers used as sieving separation media for the fluorescently labeled DNA fragments, the low number of samples which could be analyzed in parallel, and the difficulty of total automation of the sample preparation methods. These limitations shifted focus to develop techniques without gels allowing sequence determination on very large numbers of samples in parallel.

454 Genome Sequencer FLX instrument made by Roche Applied Science. The first 'next generation' sequencing system on the market was developed by 454 Life Sciences and introduced in 2005. Within this instrument, DNA fragments are ligated with specific adapters that cause the binding of one fragment to a bead. Emulsion PCR is carried out for fragment amplification, with water droplets containing one-bead and PCR reagents immersed in oil. Amplification is needed to obtain sufficient light signal intensity for reliable detection in the so-called 'sequencing-by-synthesis' reaction steps. When PCR amplification cycles are completed and after denaturation, an individual bead with a single amplified fragment is placed at the top end of an etched fiber in an optical fiber chip, created from a glass fiber bundle. Each glass fiber serves as optical waveguide, which transfers light to its other end attached to a CCD camera, enabling positional detection of emitted light. Therefore, each bead has an addressable position in the light guide chip, containing hundreds of thousands of available positions. In a subsequent step, polymerase enzyme and primer are added to each of the beads, along with one unlabeled nucleotide per bead, thus starting the synthesis of the complementary strand. The incorporation of the following base by the polymerase enzyme in the growing chain releases a pyrophosphate group, which is then detected as emitted light. This method has achieved DNA read length to the 400-500 base range, with paired end reads. Drawbacks to this method are a relatively high cost of operation and generally lower reading accuracy in homopolymer stretches of identical bases and generally lower reading accuracy in homopolymer stretches of identical bases.

Illumina (Solexa) Genome Analyzer: The Solexa sequencing platform was first commercialized in 2006, and was acquired by Illumina in 2007. The functioning principles of this instrument are based on the same sequencing-by-synthesis chemistry. DNA fragments are ligated at both ends to adapters and, after denaturation, immobilized at one end on a solid support. The surface of the support is coated densely with the adapters and the complementary adapters. Each single-stranded fragment, immobilized at one end on the surface, creates a 'bridge' structure by hybridizing with its free end to the complementary adapter on the surface of the support. In the mixture containing the PCR amplification reagents, the adapters on the surface act as primers for the PCR amplification. PCR amplification is needed as a step in this system as well to ensure sufficient light signal intensity for reliable detection of added bases. The PCR step creates clusters of single-stranded DNA fragments on the surface of the support called 'polonies'. The novelty of this system occurs in the next step following amplification, where the reaction mixture for the sequencing reactions and DNA synthesis is supplied onto the surface and contains primers, four reversible terminator nucleotides each labeled with a different fluorescent dye and the DNA polymerase. After incorporation into the DNA strand, the terminator nucleotide, as well as its position on the support surface, is detected and identified by its fluorescent dye at the CCD camera. This system achieved sequence read lengths of approximately 35 nucleotides, and the sequence of 40 million polonies can be simultaneously determined in parallel. Updates to the Illumina system have been the introduction of a paired-end module, new optics and camera components that allowed the system to triple the output per paired-end run from 1 to 3 Gb of data [32].

Applied Biosystems ABI SOLiD system: ABI introduced the SOLiD system in 2007 uses ligation chemistry as its primary platform. In this technique, DNA fragments are ligated to adapters then bound to beads. A water droplet in oil emulsion contains the amplification reagents and only one fragment bound per bead; DNA fragments on the beads are amplified by emulsion PCR. Once amplified, the DNA are denatured After DNA, and the beads are deposited onto a glass support surface. In the next steps, a primer is hybridized to the adapter, followed by the hybridization of a mixture of oligonucleotide octamers followed by the addition of the ligation mixture. Utilizing four unique fluorescent labels and repeated series of hybridization and ligations cycles, the DNA sequence is determined by interrogating every 1st and 2nd base in each ligation reaction. Multiple cycles of ligation, detection and cleavage are performed with the number of cycles determining the eventual read length of the DNA strand. The sequencing process may be continued in the same way with another primer shorter by one base than the previous one, and in fact is done so five times. Through this primer 'reset' process, theoretically every base is interrogated in two independent ligation reactions by two different primers. Thus, the sequence read length is shorter, respectively speaking, at about 35 bases. However, the method has proven to be very accurate as a result of this dual interrogation type format.

Non-Optical Methods of Genome Sequencing: The previously outlined optical based methods are still hindered by relatively large reaction volume size needed to prepare templates that are detectable by theses systems, the need for special nucleotide analogues as reagents, and complicated enzymatic and/or chemiluminescence reactions to generate detectable optical signals. As a result of these limitations, a major shift towards non-optical based sequencing methods occurred, resulting in the development of sequencing techniques with two other major categories of detection schemes; sequencing based mass spectrometry, and sequencing based on integrated circuits.

Nucleic Acid Sequencing based on Mass Spectrometry: In U.S. Pat. No. 7,501,251, methods are described for detecting a target nucleic acid in a biological sample using RNA amplification using a primer comprising a sequence that is complementary to a polynucleotide sequence in the target nucleic acid, and a sequence that encodes an RNA polymerase promoter. The RNA polymerase that recognizes the promoter is used to synthesize RNA. The newly synthesized RNA is detected by mass spectrometry, which establishes the presence or absence of that target RNA in the biological sample. The detection systems of mass spectrometers provide a means of determining the individual mass and charge of volatilized molecules in a vacuum as the trajectory of the 'flying' molecule is influenced by combinations of electric and magnetic fields. This technique is an example of MS-based proteomics; a discipline made possible by the availability of gene and genome sequence databases and technical and conceptual advances primarily in the area of protein ionization methods.

Nucleic Acid Sequencing using integrated semiconductor devices. Recent advances in the field of photonic imaging have produced very large, fast arrays of electronic sensors. This technology was adapted for the construction of an integrated circuit to detect the hydrogen ions that would be released by NNA polymerase during sequencing by synthesis rather than a sensor designed for the detection of a photon[34]. The Ion Torrent was developed by Life Technologies using the ion-sensitive field-effect transistor (IS-FET) due to its sensitivity to hydrogen ions and compatibility with CMOS processes [35]. The Ion Torrent was not the first effort to detect both single-nucleotide polymorphisms [36], monitor DNA synthesis [37], or electronically sequence DNA[38]. None of these earlier attempts were able to produce de novo DNA sequence, address issues of delivering template NDA to the sensors, or scale the entire system to large arrays [35]. Prior to the Ion Torrent, ISFETs were limited in the number of sensors per array, the yield of working independent sensors and readout speed [39], and had issues protecting the electronic circuitry from fluid once the sensors were exposed [40]. With this new technology, 25 million bases can be generated from chips containing 1.2 million sensors. This capability was demonstrated in by Rothberg et. al [35].

U.S. Pat. No. 7,948,015 focuses on the development of the ion sensor chips, supporting instrumentation, and software to enable de novo DNA sequencing for applications requiring millions to billions of bases. The method described here will utilize universal or broad range primers and individual sample specific barcodes or tags as have been well described in the literature, in order to analyzed batches or multiple specific specimens or subjects or sample detecting many specific targets that are grouped together to create a single assay. This assay will be analyzed using a cost effective semi-conductor technology or other non-optical method for determining the sequence of molecular material such as proteins or nucleic acids (RNA or DNA). One example is to sequence each of the multiplexed analytes based upon pH generation detected using a semi-conductor or other chip-based technology. This allows many analytes to be screened all at once using broad range (e.g. kingdom specific, genus specific, family or class or sub-groups of organisms or targets) to be screened all at once and allows many different samples to be analyzed all together.

SUMMARY OF THE INVENTION

The present invention includes provide methods, compositions, and workflows, or components thereof, devices and methods based upon non-optical sequencing processes that improve and reduce the cost of genetic evaluation of microbial populations and ecologies in any environment, and further provide the ability to perform comprehensive microbial population characterization in a system that directs treatments or remedies or enhancements or remediations, thereby these embodiments will make such treatments, remedies or enhancements or remediations specific to the subject or the environment and the needed therapeutic trajectory to enhance the health and efficiency of a given animal, human or environmental system. To target and enhance the specific delivery of the treatment more convenient, targeted, and effective methods based upon lower cost diagnostic and microorganism evaluation. These combined benefits cascade to provide improved analytical efficiency, analytical accuracy, treatment efficiency, treatment accuracy, and treatment outcomes, while limiting errors in treatment, remedy, remediation or enhancement. The present invention provides a universal, sensitive and ubiquitous method that uses non-optical nucleic acid sequencing methods and universal gene targets (targets that are universal among all microorganisms such as the 16s gene for archaea and bacteria and the 18s gene for fungi, and the ITS gene for fungi) for determining the presence and/or amount of nucleic acids, thus detecting and determining the identity of microorganisms from any algal, archaeal, bacterial, fungal or parasitical species in any sample suspected of containing said nucleic acids.

The present invention can be used to investigate, define, or discover from an antimicrobial agents resistance gene, and optionally, from antimicrobial agents toxin gene the detected and identified organisms chemical sensitivities and drug susceptibilities.

In one embodiment, the present invention includes a method for determining the identify of an organism or virus in a sample comprising the steps of: isolating DNA or RNA from the sample; combining the DNA or RNA directly or with one or more universal or target specific amplification primers, wherein the one or more primers are specific for one or more group of target microorganisms or virus; amplifying the DNA, or the RNA following reverse transcription with a reverse transcriptase; and contacting the amplification product with one or more species-, organism- or virus-specific detectable marker. In one aspect, the species-, organism- or viral particle-specific detectable marker is selected from a tag, label, or barcode. In another aspect, the amplification product is further sequenced with a non-optical nucleic acid sequencer. In another aspect, the organism is defined further as a bacteria and the universal primers are specific for 16S ribosomal nucleic acids. In another aspect, the organism is defined further as a fungi and the universal primers are specific for 18S ribosomal nucleic acids. In another aspect, the organism is defined further as a fungi and the universal primers are specific for ITS nucleic acids. In another aspect, the universal primers are specific for at least one of 23s ribosomal nucleic acids, nirS, rpoB, COX1, rbcL, LSU, 28S, fusA, ileS, lepA, leuS, pyrG, recA, recG, rplB, or SSU. In another aspect, the step of amplification comprises PCR or linear amplification followed by non-optical sequencing of amplicons or direct non-optical sequencing or DNA and RNA to identify microorganisms. In another aspect, primers are universal primers selected for a single specific species, wherein amplification and detection of a product is species specific. In another aspect, the method further comprises the step of enriching the DNA or RNA using at least one of magnetic bead hybridization, precipitation, PCR, multiplex PCR, or RT-PCR. In another aspect, the primers for the step of amplifying the DNA, or the RNA following reverse transcription with a reverse transcriptase are selected from SEQ ID NOS.: 1 to 283. In another aspect, the primers are universal primers and the method further includes the steps of detecting and identifying unknown, novel or previously unidentified microorganisms using non-optical sequencing. In another aspect, the primers are universal primers or organism specific primers and the method further includes the steps of detecting and identifying known or suspected microorganisms using non-optical sequencing. In another aspect, the method further comprises the step of using non-optical sequencing to identify and quantitate microorganisms. In another aspect, the method further comprises the step of using non-optical sequencing to diagnose an environmental, industrial, veterinary, or medical sample for microorganisms that are either known, suspected, unknown, novel, or previously unidentified. In another aspect, the method further comprises the step of using non-optical sequencing to characterize the microbiological composition of an environmental, industrial, veterinary, or medical sample. In another aspect, the method further comprises the step of generating a report using non-optical sequencing to determine the relative percentage of microorganisms in an environmental, industrial, veterinary, or medical sample and based on those finding selecting at least one of a treatment, a therapy, an improvement, or a remediation.

Another embodiment of the present invention includes a method for determining the identify of an organism or virus in a sample comprising the steps of: isolating a DNA or RNA from the sample; combining the DNA or RNA with one or more universal amplification primers, wherein the one or more primers are specific for one or more target organisms or virus; amplifying the DNA, or the RNA following reverse transcription with a reverse transcriptase; and sequencing the amplified products with a non-optical nucleic acid sequencer. In one aspect, the method further comprising the step of contacting the amplification product with a species-, organism- or virus-specific detectable marker is selected from a tag, label, or barcode. In another aspect, the organism is defined further as a bacteria and the universal primers are specific for 16S ribosomal nucleic acids. In another aspect, the organism is defined further as a fungi and the universal primers are specific for 18S ribosomal nucleic acids. In another aspect, the organism is defined further as a fungi and the universal primers are specific for ITS nucleic acids. In another aspect, the step of amplification comprises PCR or linear amplification. In another aspect, the primers are universal primers selected for a single specific species, wherein amplification and detection of any product will be species specific. In another aspect, the method further comprises the step of enriching the DNA or RNA using at least one of magnetic bead hybridization, precipitation, PCR, multiplex PCR, or RT-PCR. In another aspect, the universal primers are specific for at least one of 23s ribosomal nucleic acids, nirS, rpoB, COX1, rbcL, LSU, 28S, fusA, ileS, lepA, leuS, pyrG, recA, recG, rplB, or SSU. In another aspect, the primers for the step of amplifying the DNA, or the RNA following reverse transcription with a reverse transcriptase are selected from SEQ ID NOS.: 1 to 283. In another aspect, the primers are universal primers and the method further includes the steps of detecting and identifying unknown, novel or previously unidentified microorganisms using non-optical sequencing. In another aspect, the primers are universal primers or organism specific primers and the method further includes the steps of detecting and identifying known or suspected microorganisms using non-optical sequencing. In another aspect, the non-optical sequencer is used to identify and quantitate microorganisms. In another aspect, the non-optical sequencer is used to diagnose an environmental, industrial, veterinary, or medical sample for microorganisms that are either known, suspected, unknown, novel, or previously unidentified. In another aspect, the non-optical sequencer is used to characterize the microbiological composition of an environmental, industrial, veterinary, or medical sample. In another aspect, the method further comprised the step of determining the relative percentage of microorganisms in an environmental, industrial, veterinary, or medical sample. In another aspect, the method further comprises the step of generating a report using non-optical sequencing to determine the relative percentage of microorganisms in an environmental, industrial, veterinary, or medical sample and based on those finding selecting at least one of a treatment, a therapy, an improvement, or a remediation.

BRIEF DESCRIPTION OF THE DRAWINGS

For a more complete understanding of the features and advantages of the present invention, reference is now made to the detailed description of the invention along with the accompanying FIGURE and in which:

FIG. 1 shows the non-optical genetic sequencing method and system for evaluation of microorganisms from a variety of sources of the present invention.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention relates generally to an approach that utilize non-optical genetic sequencing methods for diagnosing and evaluating microorganisms in any sample type including human, animal, and environmental samples. Such diagnostic methods can be done using specific assays for universal and more specific gene targets (targets that are universal among all microorganisms such as the 16s gene for Achaea and bacteria and the 18s gene for fungi, and the ITS gene for fungi or more specific genes such as nuclease genes for virus species) for detecting the presence of and determining the identity and relative abundance of microorganisms, including protozoa, fungi, archaea, bacteria and viruses in any given sample. This non-optical method of sequencing DNA is more cost effective than all optical sequencing methods used to date, thereby applying novel technological innovation to microbial diagnostic application whereby we are decreasing the cost of diagnosing and evaluating human, animal and environmental samples of all kinds and thereby increasing the utility and applicability of such diagnostics for a variety of purposes. The present invention is directed to the resolution of the complete microbial communities of etiologic agents and commensal flora present in samples including, but not limited to, animals, humans, environmental, clinical, or other samples, including samples of unknown origin from which knowledge of the complete microbial community is of scientific and/or medical interest. This method is also able to detect and help identify novel pathogens. The invention is further directed to the determination of detailed genetic information about the individual organisms which are detected and identified that make up in the sample's microbiome including identification of genes that predict or indicate sensitivity or susceptibility of the organism to antimicrobials, antibiotics, or other chemical compounds, ions, or elements.

Presently, the fastest bacterial identification system, the autoSCAN-Walk-Away system (Dade Behring) identifies both gram-negative and gram-positive bacteria species from standardized inoculums in as little as 2 hours, and gives susceptibility patterns to most antibiotics in 5 to 6 hours. However, this system has a particularly high percentage (i.e. 3.3 to 40.5%) of non-conclusive identifications with bacterial species other than Enterobacteriaceae [2]. Enterobacteriaceae, the percentage of non-conclusive identifications was 2.7 to 11.4%. The following list of microorganisms identified by commercial systems based on classical identification methods: Aeromonas caviae Aeromonas hydrophila and A. sobria Citrobacter amalonaticus Citrobacter diversus Citrobacter freundii Edwardsiella tarda Enterobacter aerogenes Enterobacter agglomerans Enterobacter asburiae Enterobacter cloacae Escherichia coli Hafnia alvei Klebsiella oxytoca Klebsiella pneumoniae Klebsiella rhinoscleromatis Kuyvera spp. Morganella morganii Proteus mirabilis Proteus penneri Proteus vulgaris Providencia alcalifaciens Providencia rettgen Providencia stuartii Salmonella spp.; Serratia liquefaciens Serratia marcescens Serratia odonifera Serratia rubidaea Shigella flexneri Shigella sonnei; Pseudomonas aeruginosa; Acinetobacter calcoaceticus; and Xanthomonas maltophilia.

A wide variety of bacteria and fungi are routinely isolated and identified from clinical specimens in microbiology laboratories. The following lists of the most commonly isolated bacterial and fungal pathogens from various types of clinical specimens. These pathogens are the main organisms associated with nosocomial and community-acquired human infections and are therefore considered the most clinically important.

Examples of Pathogenic Bacteria that can be detected using the present invention include: Abiotrophia defective; Achromobacter piechaudii; Achromobacter xylosoxidans; Acinetobacter beijerinckii; Acinetobacter calcoaceticus; Acinetobacter haemolyticus; Acinetobacter seohaensis; Acinetobacter iwoffii; Acinetobacter johnsonii; Acinetobacter junii; Acinetobacter septicus; Acinetobacter ursingii; Actinomyces odontolyticus; Aerococcus sanguinicola; Aerococcus viridians; Aggregatibacter segnis; Alistipes finegoldii; Anaplasma phagocytophila; Anaplasma phagocytophilum; Arcobacter cryaerophilus; Atopobium rimae; Babesia divergens; Babesia duncani; Babesia microti; Bacillus pumilus; Bacteroides thetaiotaomicron; Bacteroides vulgatus; Bartonella australis; Bartonella bacilliformis; Bartonella clarridgeiae; Bartonella coopersplainsensis; Bartonella doshiae; Bartonella grahamii; Bartonella henselae; Bartonella koehlerae; Bartonella quintana; Bartonella rochalimae; Bartonella tamiae; Bartonella vinsonii; Bartonella washoensis; Bergeyella zoohelcum; Bordetella pertussis; Borrelia afzelii; Borrelia burgdorferi; Borrelia garinii; Borrelia hermsii; Borrelia lonestari; Borrelia parkeri; Borrelia valasiana; Brachyspira aalborgi; Brachyspira hyodysenteriae; Bracyspira hyodysenteriae; Brevinema; Brevundimonas vesicularis; Brucella abortus; Brucella canis; Brucella melitensis; Brucella suis; Burkholderia cenocepacia; Burkholderia gladioli; Campylobacter jejuni; Capnocytophaga sputigena; Cardiobacterium hominis; Cellulosimicrobium cellulans; Chlamydia pneumoniae; Chlamydia trachomatis; Chlamydophila psittaci; Clostridium botulinum; Clostridium difficile; Clostridium perfringens; Clostridium tetani; Corynebacterium confusum; Corynebacterium diphtheriae; Corynebacterium jeikeium; Corynebacterium mucifaciens; Corynebacterium striatum; Corynebacterium ureicelerivorans; Coxiella burnetii; Coxiella burnetti; Cristispira; Dermabacter hominis; Dialister pneumosintes; Dolosigranulum pigrum; Ehrlichia chaffeensis; Ehrlichia ewingii; Enterobacter aerogenes, Raoultella ornithinolytica; Enterobacter cloacae; Enterococcus faecalis; Enterococcus faecium; Exiguobacterium acetylicum; Facklamia hominis; Francisella tularensis; Fusobacterium canifelinum; Fusobacterium gonidiaformans; Gemella morbillorum; Gordonia polyisoprenivorans; Gordonia sputi; Gordonia terrae; Granulicatella adiacens; Granulicatella elegans; Haemophilus influenzae; Haemophilus segnis; Kluyvera cryocrescens; Kocuria rosea; Kytococcus schroeteri; Legionella pneumophila; Leptonema; Leptospira biflexa; Leptospira borgpetersenii; Leptospira interrogans; Leptospira kirschneri; Leptospira wolbachii; Leptotrichia buccalis; Leptotrichia trevisanii; Listeria monocytogenes; Morganella morganii; Mycobacterium leprae; Mycobacterium tuberculosis; Mycobacterium ulcerans; Mycoplasma fermentans; Mycoplasma hyopharyngis; Mycoplasma pneumoniae; Mycoplasma timone; Neisseria elongata; Neisseria flavescens; Neisseria gonorrhoeae; Neisseria meningitidis; Neisseria pharyngis; Neisseria subflava; Ochrobactrum anthropi; Paludibacter propionicigenes; Pantoea agglomerans; Parabacteroides goldsteinii; Prevotella buccae; Pseudomonas aeruginosa; Pseudomonas fulva; Pseudomonas luteola; Rahnella aquatilis; Raoultella ornithinolytica; Rickettsia; Rickettsia spp; Rothia mucilaginosa; Rothia nasimurium; Salmonella typhi; Salmonella typhimurium; Selenomonas artemidis; Selenomonas sputigena; Serratia liquefaciens; Serratia marcescens; Shewanella putrefaciens; Solobacterium moorei; Sphingobacterium multivorum; Sphingomonas paucimobilis; Spirillum minus; Spironema; Staphylococcus aureus; Staphylococcus caprae; Staphylococcus epidermidis; Staphylococcus haemolyticus; Staphylococcus hominis; Staphylococcus lugdunensis; Staphylococcus pasteuri; Staphylococcus saprophyticus; Stenotrophomonas maltophilia; Streptococcus agalactiae; Streptococcus canis; Streptococcus constellatus; Streptococcus cristatus; Streptococcus dysgalactiae; Streptococcus gallinaceus; Streptococcus gallolyticus; Streptococcus gordonii; Streptococcus infantarius; Streptococcus mitis; Streptococcus oligofermentans; Streptococcus oralis; Streptococcus pneumonia; Streptococcus pneumoniae; Streptococcus pseudopneumoniae; Streptococcus pyogenes; Streptococcus salivarius; Streptococcus sanguinis; Treponema carateum; Treponema denticola; Treponema pallidum; Treponema pertenue; Veillonella dispar; Veillonella montpellierensis; Veillonella parvula; Vibrio cholerae; and Yersinia pestis.

Examples of Pathogenic Fungi that can be detected using the present invention include: Examples of Pathogenic Fungi; Aspergillus aculeatus; Aspergillus alliaceus; Aspergillus caesiellus; Aspergillus caespitosus; Aspergillus candidus; Aspergillus carneus; Aspergillus clavatus; Aspergillus clavatus; Aspergillus deflectus; Aspergillus egyptiacus; Aspergillus fischerianus; Aspergillus flavus; Aspergillus flavus; Aspergillus foetidus; Aspergillus fumigatus; Aspergillus fumigatus; Aspergillus glaucus; Aspergillus nidulans; Aspergillus niger; Aspergillus ochraceus; Aspergillus oryzae; Aspergillus parasiticus; Aspergillus penicilloides; Aspergillus restrictus; Aspergillus sojae; Aspergillus sydowii; Aspergillus tamari; Aspergillus terreus; Aspergillus ustus; Aspergillus versicolor; Candida albicans; Candida amphixiae; Candida antarctica; Candida argentea; Candida ascalaphidarum; Candida atlantica; Candida atmosphaerica; Candida blattae; Candida carpophila; Candida carvajalis; Candida cerambycidarum; Candida chauliodes; Candida corydali; Candida dosseyi; Candida dubliniensis; Candida ergatensis; Candida fermentati; Candida fructus; Candida glabrata; Candida guilliermondii; Candida haemulonii; Candida insectamens; Candida insectorum; Candida intermedia; Candida jeffresii; Candida kefyr; Candida krusei; Candida lusitaniae; Candida lyxosophila; Candida maltosa; Candida marina; Candida membranifaciens; Candida milleri; Candida oleophila; Candida oregonensis; Candida parapsilosis; Candida quercitrusa; Candida rugosa; Candida sake; Candida shehatea; Candida sinolaborantium; Candida sojae; Candida subhashii; Candida temnochilae; Candida tenuis; Candida theae; Candida tropicalis; Candida tsuchiyae; Candida utilis; Candida viswanathii; Cryptococcus neoformans; Histoplasma capsulatum; Histoplasma duboisii; Pneumocystis jirovecii; Stachybotrys albipes; Stachybotrys alternans; Stachybotrys breviuscula; Stachybotrys chartarum; Stachybotrys chlorohalonata; Stachybotrys cylindrospora; Stachybotrys dichroa; Stachybotrys elegans; Stachybotrys eucylindrospora; Stachybotrys freycinetiae; Stachybotrys kampalensis; Stachybotrys kapiti; Stachybotrys longispora; Stachybotrys mangiferae; Stachybotrys microspora; Stachybotrys nephrodes; Stachybotrys nephrospora; Stachybotrys nilagirica; Stachybotrys oenanthes; Stachybotrys parvispora; Stachybotrys ruwenzoriensis; Stachybotrys sansevieriae; Stachybotrys sinuatophora; Stachybotrys suthepensis; Stachybotrys theobromae; and Stachybotrys waitakere.

Definitions

As used herein, the term "prepared or isolated from" when used in reference to polynucleotides "prepared or isolated from" a pathogen refers to both polynucleotides (e.g., DNA or RNA, including cDNA produced therefrom) extracted and/or purified from a microorganism, and to polynucleotides that are copied from the transcriptosome of a microorganism, e.g., by a process of reverse-transcription or DNA polymerization using native DNA or RNA as a template. Polynucleotides of the pathogen may be isolated from a specimen in conjunction with host nucleic acid.

As used herein, the term "Pathogen" refers to a microorganism, which causes disease in another organism (e.g., animal or plant) by directly infecting the other organism, or by producing agents that causes disease in another organism (e.g., bacteria that produce pathogenic toxins and the like). As used herein, pathogens include, but are not limited to bacteria, protozoa, fungi (e.g., molds and yeasts), helminths (e.g., cestodes, nematodes and trematodes), viroids and viruses, or any combination thereof, wherein each pathogen is capable, either by itself or in concert with another pathogen, of eliciting disease in vertebrates including but not limited to mammals, and including but not limited to humans. As used herein, the term "pathogen" also encompasses microorganisms, which may not ordinarily be pathogenic in a non-immunocompromised host. Specific nonlimiting examples of bacterial pathogens include [list species that were discovered to be in wounds by your invention]. Specific nonlimiting examples of viral pathogens include Herpes simplex virus (HSV)1, HSV2, Epstein Barr virus (EBV), cytomegalovirus (CMV), human Herpes virus (HHV) 6, HHV7, HHV8, Varicella zoster virus (VZV), hepatitis C, hepatitis B, adenovirus, Eastern Equine Encephalitis Virus (EEEV), West Nile virus (WNE), JC virus (JCV), and BK virus (BKV). Fungi such as Candida spp, Aspergillus spp., Cryptococcus spp, Histoplasma spp, Pneumocystis spp, and Stachybotrys spp. Helminths such as schistosoma spp, Paragonimus spp, Trichenella spp. Taenia spp., Cchinococcus spp. Hymenolepis spp, Strongyloides spp, Dracunculus spp. Protozoa such as Cryptosporidium spp, Encephalitozoon spp., Giardia spp., Plasmodium spp., Phytophthora spp., and Kneallhazia spp., etc.

As used herein, the term "Microorganism" includes prokaryotic and eukaryotic microbial species from the Domains of Archaea, Bacteria, and Eucarya, the latter including yeast and filamentous fungi, helminths, protozoa, algae, or higher Protista. The term "microbe" is used interchangeably with the term microorganism.

As used herein, the terms "Bacteria" or "Eubacteria" refers to a domain of prokaryotic organisms. Bacteria include at least 11 distinct groups as follows: (1) Gram-positive (gram+) bacteria, of which there are two major subdivisions: (i) high G+C group (Actinomycetes, Mycobacteria, Micrococcus, others) (ii) low G+C group (Bacillus, Clostridia, Lactobacillus, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) Bacteroides, Flavobacteria; (7) Chlamydia; (8) Green sulfur bacteria; (9) Green nonsulfur bacteria (also anaerobic phototrophs); (10) Radioresistant micrococci and relatives; (11) *Thermotoga* and *Thermosipho thermophiles*.

As used herein, the term "Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

As used herein, the term "Gram-positive bacteria" include cocci, nonsporulating rods, and sporulating rods. The genera of Gram-positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

As used herein, the term "Detection" refers to the at least qualitative determination of the presence or absence of a microorganism in a specimen. The term "identification" also includes the detection of a microorganism, i.e., determining the genus, species, or strain of a microorganism according to its recognized taxonomy in the art and as described in the present specification. The term "identification" further includes the quantification of a microorganism in a specimen, e.g., the copy number of the microorganism in a microliter (or a milliliter or a liter) or a microgram (or a milligram or a gram or a kilogram), or swab or any other type or quantity of any type of specimen containing or suspected of containing microorganisms.

As used herein, the term "Immunocompromised subject or individual" refers to an individual who is at risk for developing infectious diseases, because the immune system of the individual is not working at optimum capacity. In one aspect, the individual is immunocompromised due to a treatment regimen designed, for example, to prevent inflammation or to prevent rejection of a transplant.

As used herein, the term "Specimen" refers to a biological material or environmental sample from any source containing or suspected of containing 1 or more microorganisms of any type which can be evaluated for the microbiological presence of microorganisms, which is isolated from its natural environment (including the body such as skin, mucosa, internal organs, and fluids or a body cavity collected by lavage, water, soil, feces, etc) and contains a polynucleotide DNA or RNA. A biological fluid includes, but is not limited to, blood, plasma, serum, sputum, urine, pus or other wound exudate, infected tissue sampled by wound debridement or excision, cerebrospinal fluid, lavage, and leucopoiesis specimens, for example. A specimen may also be an environmental specimen such as soil, water, or animal or human waste to detect the presence of a pathogen in an area where an outbreak of disease related to a specific pathogen has occurred. A specimen may also be obtained from a tissue bank or other source for the analysis of archival samples or to test samples prior to transplantation. A specimen useful in the method described herein may be any plant, animal, bacterial or viral material containing a polynucleotide, or any material derived there from.

A specimen is suspected of containing at least one of a plurality of known or unknown or potential or opportunistic pathogens or commensal organisms for any of a number of reasons. For example, a soil specimen may be suspected of containing a pathogen if humans or animals living close to the location where the soil specimen was collected show symptoms of a condition or diseases associated with a soil pathogen. Few environments and therefore few specimens are sterile and do not contain some type of microorganism. Thus, a specimen is any collection of source material sampled from any environment. Specimens taken from such a subject may be suspected of containing at least one of a plurality of known unknown, suspected, opportunistic or potential pathogens or commensal organisms, even in the absence of infection.

As used herein, the term "Reverse transcript" refers to a DNA complement of an RNA strand generated by an RNA-dependent DNA polymerase activity.

As used herein, the term primer pair "capable of mediating amplification" is understood as a primer pair that is specific to a target polynucleotide, has an appropriate melting temperature, and does not include excessive secondary structure. Guidelines for designing primer pairs capable of mediating amplification are well documented in the literature. The present invention can also take advantage of a single specific primer for amplification.

As used herein, the term "Conditions that promote amplification" are the conditions for target amplification provided by the manufacturer for the enzyme used for amplification of template. It is understood that an enzyme may work under a range of conditions (e.g., buffer pH, ion concentrations, temperatures, concentrations of enzyme or target). It is also understood that several temperatures may be required for amplification (e.g., three in PCR for annealing primer to template, extending primer as the complement of template, and denaturing extended primer from template). Conditions that promote amplification need not be identical for all primers and targets in a reaction, and reactions may be carried out under suboptimal conditions where amplification is still possible.

As used herein, the term "aliquot" refers to a sample volume taken from an amplification reaction mixture. The volume of an aliquot can vary, but will generally be constant within a given experimental run. An aliquot will be less than the volume of the entire reaction mixture. Where there are X aliquots to be withdrawn during an amplification regimen, the volume of an aliquot will be less than or equal to 1/X times the reaction volume.

As used herein, the term "Dispense" means to dispense, transfer, withdraw, extrude or remove. As used herein, the phrase "dispensing an aliquot from the reaction mixture at plural stages" refers to the withdrawal of an aliquot at least twice, and preferably at least about 3, 4, 5, 10, 15, 20, 30 or more times during an amplification reaction. A "stage" will refer to a point at or after a given number of cycles, or, where the amplification regimen is non-cyclic, will refer to a selected time at or after the initiation of the reaction.

As used herein, the term "Separating" nucleic acids in a sample refers to a process whereby they are separated by size (i.e., length). The method of separation should be capable of resolving nucleic acid fragments that differ in size by ten nucleotides or less (or, alternatively, by ten base pairs or less, e.g., where non-denaturing conditions are employed). Preferred resolution for separation techniques employed in the methods described herein includes resolution of nucleic acids differing by five nucleotides or less (alternatively, five base pairs or less), up to and including resolution of nucleic acids differing by only one nucleotide (or one base pair).

As used herein, the term "Size distinguishable by capillary electrophoresis" refers to a difference of at least one nucleotide (or base pair), but preferably at least 5 nucleotides (or base pairs) or more, up to and including 10 nucleotides (or base pairs) or more. As used herein, the term "distinct from" when used in reference to the length of a polynucleotide means that the length of the polynucleotide is distinguishable from the length of another by capillary electrophoresis. Other apparati and methods for separation of polynucleotides by their length can be used as long as they are capable of resolving a difference of at least one nucleotide (or base pair), but preferably at least 5 nucleotides (or base pairs) or more, up to and including 10 nucleotides (or base pairs) or more.

As used herein, the term "Amplified product" refers to polynucleotides that are copies of a particular polynucleotide, produced in an amplification reaction. An "amplified product" according to the one embodiment, may be DNA or RNA, and it may be double-stranded or single-stranded. An amplified product is also referred to herein as an "amplicon."

As used herein, the term "Amplification" or "amplification reaction" refers to a reaction for generating a copy of a particular polynucleotide sequence or increasing the copy number or amount of a particular polynucleotide sequence. For example, polynucleotide amplification may be a process using a polymerase and a pair of oligonucleotide primers for producing any particular polynucleotide sequence, i.e., the whole or a portion of a target polynucleotide sequence, in an amount that is greater than that initially present. Amplification may be accomplished by the in vitro methods of the polymerase chain reaction (PCR). See generally, *PCR Technology: Principles and Applications for DNA Amplification* (Erlich, ed.) Freeman (1992); *PCR Protocols: A Guide to Methods and Applications* (Innis et al., eds.) Academic (1990); Mattila et al., 1991, Nucleic Acids Res. 19: 4967; Eckert et al., 1991, PCR Methods and Applications 1: 17; *PCR* (McPherson et al., eds.), IRL Press (1995); and U.S. Pat. Nos. 4,683,202 and 4,683,195, each of which is incorporated by reference in its entirety. Other amplification methods include, but are not limited to: (a) ligase chain reaction (LCR) (see Wu & Wallace, 1989, Genomics 4: 560-569 and Landegren et al., Science, 1988, 241: 1077-1080); (b) transcription amplification (Kwoh et al., 1989, Proc. Natl. Acad. Sci. USA 86: 1173-1177); (c) self-sustained sequence replication (Guatelli et al., 1990, Proc. Natl. Acad. Sci. USA, 87: 1874-1878); and (d) nucleic acid based sequence amplification (NABSA) (Sooknanan & Malek, 1995, Bio/Technology 13: 563-565), each of which is incorporated by reference in its entirety.

As used herein, the term "target polynucleotide" (including, e.g., a target RNA, target cDNA, or target DNA) refers a polynucleotide to be analyzed. A target polynucleotide may be isolated or amplified before being analyzed. For example, the target polynucleotide may be comprised of a sequence that lies between the hybridization regions of two members of a pair of oligonucleotide primers that are used to amplify the target. A target polynucleotide may be RNA or DNA (including, e.g., cDNA).

As used herein, the term "microbe-specific target polynucleotide" refers to a target polynucleotide as defined above, wherein the target polynucleotide is prepared or isolated from a specimen suspected of containing a pathogen, and which is present in only one member of the group of different pathogens that are being analyzed (i.e., the target polynucleotide has a unique sequence and is specific for detection of the pathogen's genera or species).

As used herein, the term "oligonucleotide primer" refers to a polynucleotide molecule (i.e., DNA or RNA) capable of annealing to a polynucleotide template and providing a 3' end to produce an extension product that is complementary to the polynucleotide template. The conditions for initiation and extension usually include the presence of four different deoxyribonucleoside triphosphates (dNTPs) and a polymerization-inducing agent such as a DNA polymerase or reverse transcriptase activity, in a suitable buffer ("buffer" includes substituents which are cofactors, or which affect pH, ionic strength, etc.) and at a suitable temperature. The primer as described herein may be single- or double-stranded. The primer is preferably single-stranded for maximum efficiency in amplification. "Primers" useful in the methods described herein are less than or equal to 100 nucleotides in length, e.g., less than or equal to 90, or 80, or 70, or 60, or 50, or 40, or 30, or 20, or 15, but preferably longer than 10 nucleotides in length.

As used herein, the terms "Label" or "detectable label" refer to any moiety or molecule that can be used to provide a detectable (preferably quantifiable) signal. A "labeled nucleotide" (e.g., a dNTP) or "labeled polynucleotide" is one linked to a detectable label. The term "linked" encompasses covalently and non-covalently bonded, e.g., by hydrogen, ionic, or Van der Waals bonds. Such bonds may be formed between at least two of the same or different atoms or ions as a result of redistribution of electron densities of those atoms or ions. Labels may provide signals detectable by fluorescence, radioactivity, colorimetry, gravimetry, X-ray diffraction or absorption, magnetism, enzymatic activity, mass spectrometry, binding affinity, hybridization radiofrequency, nanocrystals, and the like. A nucleotide useful in the methods described herein can be labeled so that the amplified product may incorporate the labeled nucleotide and becomes detectable. A fluorescent dye is a preferred label according to the one embodiment. Suitable fluorescent dyes include fluorochromes such as Cy5, Cy3, rhodamine and derivatives (such as Texas Red), fluorescein and derivatives (such as 5-bromomethyl fluorescein), Lucifer Yellow, IAEDANS, 7-Me.sub.2N-coumarin-4-acetate, 7-OH-4-CH.sub.3-coumarin-3-acetate, 7-NH$_2$-4-CH$_3$-coumarin-3-acetate (AMCA), monobromobimane, pyrene trisulfonates, such as Cascade Blue, and monobromorimethyl-ammoniobimane (see, for example, DeLuca, 1982, Immunofluorescence Analysis, in *Antibody As a Tool*, Marchalonis, et al., eds., Wiley, which is incorporated herein by reference).

As used herein, the term "labeled nucleotide" refers to a synthetic or biochemically derived nucleotide analog that is intrinsically fluorescent, e.g., as described in U.S. Pat. Nos. 6,268,132 and 5,763,167, Hawkins et al. (1995, Nucleic Acids Res., 23: 2872-2880), Seela et al. (2000, Helvetica Chimica Acta, 83: 910-927), Wierzchowski et al. (1996, Biochimica et Biophysica Acta, 1290: 9-17), Virta et al. (2003, Nucleosides, Nucleotides & Nucleic Acids, 22: 85-98), the entirety of each is hereby incorporated by reference. By "intrinsically fluorescent" it is meant that the nucleotide analog is spectrally unique and distinct from the commonly occurring conventional nucleosides in their capacities for selective excitation and emission under physiological conditions. For the intrinsically fluorescent nucleotides, the fluorescence typically occurs at wavelengths in the near ultraviolet through the visible wavelengths. Preferably, fluorescence will occur at wavelengths between 250 nm and 700 nm and most preferably in the visible wavelengths between 250 nm and 500 nm.

As used herein, the terms "detectable label" or "label" refer to a molecule or moiety capable of generating a detectable signal, either by itself or through the interaction with another label. The "label" may be a member of a signal generating system, and thus can generate a detectable signal in context with other members of the signal generating system, e.g., a biotin-avidin signal generation system, or a donor-acceptor pair for fluorescent resonance energy transfer (FRET) (Stryer et al., 1978, Ann. Rev. Biochem., 47: 819-846; Selvin, 1995, Methods Enzymol., 246: 300-334) or a nucleic acid-binding dye, producing detectable signal upon binding to polynucleotide (DNA or RNA molecule).

As used herein, the term "nucleotide" refers to a phosphate ester of a nucleoside, e.g., mono, di, tri, and tetra-phosphate esters, wherein the most common site of esterification is the hydroxyl group attached to the C-5 position of the pentose (or equivalent position of a non-pentose "sugar moiety"). The term "nucleotide" includes both a conventional nucleotide and a non-conventional nucleotide which includes, but is not limited to, phosphorothioate, phosphite, ring atom modified derivatives, and the like, e.g., an intrinsically fluorescent nucleotide.

As used herein, the term "conventional nucleotide" refers to one of the "naturally occurring" deoxynucleotides (dNTPs), including dATP, dTTP, dCTP, dGTP, dUTP, and dITP.

As used herein, the term "non-conventional nucleotide" refers to a nucleotide, which is not a naturally occurring nucleotide. The term "naturally occurring" refers to a nucleotide that exists in nature without human intervention. In contradistinction, the term "non-conventional nucleotide" refers to a nucleotide that exists only with human intervention. A "non-conventional nucleotide" may include a nucleotide in which the pentose sugar and/or one or more of the phosphate esters is replaced with a respective analog. Exemplary pentose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. A non-conventional nucleotide may show a preference of base pairing with another artificial nucleotide over a conventional nucleotide (see Ohtsuki et al., 2001, Proc. Natl. Acad. Sci., 98: 4922-4925). The base pairing ability may be measured by the T7 transcription assay as described in Ohtsuki et al. (2001). Other non-limiting examples of "artificial nucleotides" may be found in Lutz et al. (1998, Bioorg. Med. Chem. Lett., 8: 1149-1152); Voegel & Benner (1996, Helv. Chim. Acta 76, 1863-1880); Horlacher et al. (1995, Proc. Natl. Acad. Sci., 92: 6329-6333); Switzer et al. (1993, Biochemistry 32: 10489-10496); Tor & Dervan (1993, J. Am. Chem. Soc. 115: 4461-4467); Piccirilli et al. (1991, Biochemistry 30: 10350-10356); Switzer et al. (1989, J. Am. Chem. Soc. 111: 8322-8323), all of which are hereby incorporated by reference. A "non-conventional nucleotide" may also be a degenerate nucleotide or an intrinsically fluorescent nucleotide.

As used herein, the term "Degenerate nucleotide" refers to a nucleotide that may be able to basepair with at least two bases of dA, dG, dC, and dT. A non-limiting list of degenerate nucleotides that basepairs with at least two bases of dA, dG, dC, and dT include: inosine, 5-nitropyrole, 5-nitroindole, hypoxanthine, 6H,8H,4-dihydropyrimido[4,5c][1,2]oxacin-7-one (P), 2-amino-6-methoxyaminopurine, dPTP, and 8-oxo-dGTP.

As used herein, the term "Opposite orientation" refers to one nucleotide sequence complementary to the sense strand of a target polynucleotide template and another nucleotide sequence complementary to the antisense strand of the same target polynucleotide template. Primers with opposite orientation may generate a PCR-amplified product from matched polynucleotide template to which they complement. Two primers having opposite orientation may be referred to as a "reverse" primer and a "forward" primer.

As used herein, the term "Same orientation" refers to primers that comprise nucleotide sequences complementary to the same strand of a target polynucleotide template. Primers with same orientation will not generate a PCR-amplified product from matched polynucleotide template to which they complement.

As used herein, the terms "polynucleotide" or "nucleic acid" refer to a polyribonucleotide or polydeoxyribonucleotide, which may be unmodified RNA or DNA or modified RNA or DNA. "Polynucleotides" include without limitation single- and double-stranded polynucleotides, and embrace chemically, enzymatically, or metabolically modified forms of polymerized nucleotides, as well as chemical forms of DNA and RNA characteristic of particles and cells. A polynucleotide may be an isolated or purified polynucleotide or it may be an amplified polynucleotide in an amplification reaction.

As used herein, the term "Set" refers to a group of at least two. Thus, a "set" of oligonucleotide primers comprises at least two oligonucleotide primers. In one aspect, a "set" of oligonucleotide primers refers to a group of primers sufficient to specifically amplify a nucleic acid amplicon from each member of a plurality of target pathogens—generally, there will be a pair of oligonucleotide primers for each member of said plurality, (it is noted that these primer pairs will, in some aspects, also be used to amplify one or more competitor or internal standard templates).

As used herein, the term "Pair" refers to two. Thus, a "pair" of oligonucleotide primers are two oligonucleotide primers. When a "pair" of oligonucleotide primers are used to produce an extended product from a double-stranded template (e.g., genomic DNA or cDNA), it is preferred that the pair of oligonucleotide primers hybridize to different stand of the double-stranded template, i.e., they have opposite orientations.

As used herein, the term "Isolated" or "purified" refers to a naturally-occurring substance has been removed from its normal cellular environment or is synthesized in a non-natural environment (e.g., artificially synthesized). Thus, an "isolated" or "purified" substance may be in a cell-free solution or placed in a different cellular environment. For example, "purified" does not necessarily imply that a sequence is the only nucleotide present, but that it is essentially free (at least about 90% or 95%, up to 99-100% pure) of non-nucleotide or polynucleotide material naturally associated with it.

As used herein, the term "cDNA" refers to complementary or copy polynucleotide produced from an RNA template by the action of an RNA-dependent DNA polymerase activity (e.g., reverse transcriptase).

As used herein, the term "Complementary" refers to the ability of a single strand of a polynucleotide (or portion thereof) to hybridize to an anti-parallel polynucleotide strand (or portion thereof) by contiguous base-pairing between the nucleotides (that is not interrupted by any unpaired nucleotides) of the anti-parallel polynucleotide single strands, thereby forming a double-stranded polynucleotide between the complementary strands. A first polynucleotide is said to be "completely complementary" to a second polynucleotide strand if each and every nucleotide of the first polynucleotide forms base-paring with nucleotides within the complementary region of the second polynucleotide. A first polynucleotide is not completely complementary (i.e., partially complementary) to the second polynucleotide if one nucleotide in the first polynucleotide does not base pair with the corresponding nucleotide in the second polynucleotide. The degree of complementarity between polynucleotide strands has significant effects on the efficiency and strength of annealing or hybridization between polynucleotide strands. This is of particular importance in amplification reactions, which depend upon binding between polynucleotide strands.

As used herein, when an oligonucleotide primer is "complementary" to a target polynucleotide is if at least 50% (60%, 70%, 80%, 85%, 90%, 91%, 92%, 93%, 94%, 95%, 96%, 97%, 98% or 99%, or more) nucleotides of the primer form base pairs with nucleotides on the target polynucleotide.

As used herein, the term "analyzing" when used in the context of an amplification reaction refers to a qualitative (i.e., presence or absence, size detection, or identity etc.) or quantitative (i.e., amount) determination of a target polynucleotide, which may be visual or automated assessments based upon the magnitude (strength) or number of signals generated by the label. The "amount" (e.g., measured in μg, μmol, or copy number) of a polynucleotide may be measured by methods well known in the art (e.g., by UV absorption or fluorescence intensity, by comparing band intensity on a gel with a reference of known length and amount), for example, as described in *Basic Methods in Molecular Biology* (1986, Davis et al., Elsevier) and *Current Protocols in Molecular Biology* (1997, Ausubel et al., John Wiley). One way of measuring the amount of a polynucleotide in one embodiment is to measure the fluorescence intensity emitted by such polynucleotide, and compare it with the fluorescence intensity emitted by a reference polynucleotide, i.e., a polynucleotide with a known amount.

As used herein, the term "Capillary electrophoresis" refers to electrophoretic separation of nucleic acids in an aliquot from an amplification reaction wherein the separation is performed in a capillary tube. Capillary tubes are available with inner diameters from about 10 μm to 300 μm, and can range from about 0.2 cm to about 3 m in length, but are preferably in the range of 0.5 cm to 20 cm, more preferably in the range of 0.5 cm to 10 cm. In addition, the use of a microfluidic microcapillary (e.g., available from Caliper or Agilent) is specifically encompassed within the meaning of capillary electrophoresis.

As used herein, the term "aymptomatic" refers to an individual who does not exhibit physical symptoms characteristic of being infected with a given pathogen, or a given combinations of pathogens.

As used herein, the term "Plurality" refers to more than two, for example, 3 or more, 4 or more, 5 or more, 6 or more, 7 or more, 8 or more, 9 or more 10 or more etc.

The methods described here utilize a non-optical genetic sequencing approach that can identify, provide relative quantification, relative abundance or absolute identification/resolution of these quantitative factors of all known, unknown, suspected, commensal, opportunistic, pathogens and microorganisms within any given type of sample known or suspected to contain 1 or more microorganisms.

The methods described herein provide diagnostic, monitoring, evaluation and screening using either shotgun or non-targeted sequencing using non-optical genetic sequencing methods and procedures or utilize oligonucleotide probes and primers to amplify organism-specific, universal, or semi-universal portions of the genes or genomes of selected, specific or all pathogens (pathogens may be suspected pathogens, unknown or previously undescribed pathogens, opportunistic pathogens, commensal organisms that provide synergistic contribution to pathogenicity and polymicrobial communities that act together to create infection or subclinical disease including organisms in biofilm or any other phenotype or compilation within a sample hereafter referred to as pathogens) contained within a sample. The pathogen is selected from the group consisting of: bacteria, fungi (e.g., molds and yeasts), helminths, protozoan, viruses, and combinations thereof. Preferably, the pathogen is selected from the group consisting of: bacteria, fungi, viruses, and combinations thereof. Alternatively, the pathogen is selected from the group consisting of: bacteria, viruses, and combinations thereof. More preferably, the pathogens may be microbes belonging to at least two, at least three, at least four, at least five, at least six, at least seven, at least eight, at least nine, or at least ten different genera (especially bacterial and/or viral genera); the pathogens may be bacteria belonging to at least five, at least ten, at least 15, at least 20, at least 25, at least 30, at least 35, at least 40, at least 45, or at least 50 different species (especially bacterial and/or viral species).

The methods describe methods for evaluating an infection. An infection may be a suspected infection, subclinical infection, a potential infection, a future infection, or a past infection hereafter referred to as infection. A specimen may be from any environment including bodily fluids, feces, tissue, debrided materials, swabbed surfaces, biopsies, aqueous materials, fluids collected from any source, surfaces of any type, soil, food, etc., including any environment that contains microorganisms. A specimen is any form of content removed in whole or in part from an environment intended for analysis of microorganisms using non-optical genetic sequencing methods and apparatus for determining the genetic sequence of RNA or DNA either directly with shotgun sequencing or targeted using a set of primers in pairs or in multiplex where pairs of primers are 2 or more together. This non-optical genetic DNA and RNA sequencing is used to evaluate any type of sample suspected to contain or known to contain microorganisms. Such sample is hereafter referred to as a specimen.

Diagnostic, screening, monitoring, or testing for microorganisms or microbial pathogens causing an infection or microorganisms hindering or enhancing an ecological or industrial process is typically conducted for a subjects or environments or industrial processes who present symptoms characteristic of clinical infection presumably by one or more pathogenic microorganisms, or in a subject who has been in contact with another having one or more pathogenic infections, or in a subject who are otherwise suspected to have developed an infectious disease resulting from one or more pathogens or a process that has a microorganism causing contamination or fouling or improvement or enhancement or remediation of an infection, industrial process, or improvement of ecological processes or environmental improvements that can be monitored for microorganisms.

Many pathogens causing an infection or present in a specimen may be unknown. The literature suggests that only 5%-10% of microorganisms have been characterized and fully identified. Non-optical genetic sequencing may be utilized to target these known pathogens or pathogen panels identified by molecular survey as prevalent in a particular environment utilizing a multiplex, parallel or panel format allowing such pathogens to be detected and quantified rapidly. The unknown organisms can be detected, and their relationship to known organisms defined, allowing a previously unrealized ability to define infections caused by unknown microorganisms.

FIG. 1 shows the non-optical genetic sequencing evaluation detection method and system for the identification of microorganisms from a variety of sources. FIG. 1 shows the methods and use of the present invention in the field of diagnosing and monitoring industrial and environmental microbial processes, medical and veterinary diagnosis and medical and veterinary treatment, and more particularly, to universal or broad range assays and multi-tag sample specific diagnostic process using non-optical sequencing. The skilled artisan will recognize that the present invention can be used to detect and/or identify a wide variety of nucleic acid containing samples.

FIG. 1 begins with the isolation of a sample that contains a biological material that includes any type of nucleic acid at step 20. Non-limiting examples of samples include but are not limited to industrial processing, bioreactors, waste and wastewater 10, samples from human samples 12, veterinary samples 14, airborne samples 16 (e.g., filters containing biological samples such as pollen or viruses), or other environmental samples 18 that may include molds, soil samples, etc. Samples containing or suspected of containing microorganisms undergo DNA or RNA extraction at step 22, after which DNA or RNA is sequenced directly or as part of a process that uses barcoding of universal or targeted amplicons derived from PCR. In this example, the sample obtained from step 22 is further processed on sequencing beads at step 24, which the skilled artisan would understand to be an optional step. Rather than going through optical (more expensive and time consuming) genetic sequencing the DNA is sequencing using a non-optical genetic sequencing method at step 26. In this example, the detection of pH changes as hydrogen atoms are released and detected by semi-conductor based pH meters is measured at the signal and the nucleic acid sequence is determined at step 28. As nucleotides are flowed in any order of A, T, G, C when an A is added to the sequencing strand it releases a H+ ion which creates a pH change. The present invention allows the user to use very small samples to determine the nature of the nucleic acids in the sample using non-optical sequencing and provides for the first time the determination of relative amounts of virus, bacteria, fungi, etc., in a sample, the determination of which organisms are present (either as a species in general or with great detail as to the nature of the organism), can be used to quantitatively and/or qualitatively to determine the presence or absence of a wide, medium or narrow spectrum of organisms.

While quantitative monitoring of pathogens in asymptomatic individuals is not generally practical (especially using traditional methods), it can be very beneficial for subjects undergoing immunosuppressive treatment considering the accuracy and efficiency of the methodology disclosed herein. Quantitative pathogen monitoring in a subject is especially practical, if applied not as a single test for each specific infection of interest, but if applied as a controlled non-optical genetic sequencing method can be done in a cost effective an high throughput manner. Such diagnostics or monitoring can be performed on a single specimen from a subject and, preferably, as a multiplex assay for a panel of pathogens. In the case of only targeting known pathogens, assays do not represent novel panels, but combined with the benefits of a comprehensive universal diagnostic this represents a never before described format, method and technology based upon non-optical genetic sequencing of all or specific DNA and or RNA targets.

TABLE 1

The following Primers may be used with the methods of the present invention

| SEQ ID NO.: | primer | Sequence |
| --- | --- | --- |
| 1 | ecolJoinF | GACTGCGTACCAATTC |
| 2 | mseJoinR | GATGAGTCCTGAGTAA |
| 3 | 28F | GAGTTTGATCNTGGCTCAG |
| 4 | 27Fmod | AGRGTTTGATCMTGGCTCAG |
| 5 | 519Rmodbio | GTNTTACNGCGGCKGCTG |
| 6 | bac17F | GTTTGATCCTGGCTCAG |
| 7 | bac519R | GWATTACCGCGGCKGCTG |
| 8 | 27General | AGAGTTTGATYMTGGCTCAG |
| 9 | 27Bor | AGAGTTTGATCCTGGCTTAG |
| 10 | 27BIf | AGGGTTCGATTCTGGCTCAG |
| 11 | 27Chlamyd | AGAATTTGATCTTGGTTCAG |
| 12 | 27Fmod | AGRGTTTGATCMTGGCTCAG |
| 13 | bacamoA1F | GGGGTTTCTACTGGTGGT |
| 14 | bacamoA2R | CCCCTCKGSAAAGCCTTCTTC |
| 15 | Arch-amoAF | STAATGGTCTGGCTTAGACG |
| 16 | Arch-amoAR | GCGGCCATCCATCTGTATGT |

TABLE 1-continued

The following Primers may be used with the methods of the present invention

| SEQ ID NO.: | primer | Sequence |
|---|---|---|
| 17 | 189F | GGNGACTGGGACTTCTGG |
| 18 | 682R | CGSAAGAAGAGNCGSAAG |
| 19 | 661R | CCATTYCTGCAACGMGGCC |
| 20 | bacamoA1F | GGGGTTTCTACTGGTGGT |
| 21 | bacamoA2R | CCCCTCKGSAAAGCCTTCTTC |
| 22 | LinkerA | CCATCTCATCCCTGCGTGTCTCCGACTCAG |
| 23 | LinkerB | CCTATCCCCTGTGTGCCTTGGCAGTCTCAG |
| 24 | Arch-amoAF | STAATGGTCTGGCTTAGACG |
| 25 | Arch-amoAR | GCGGCCATCCATCTGTATGT |
| 26 | 341-GC-F | CGCCCGCGCCGCCCCGCGCCCGTCCCGCCGCCCCCG CCCGCCTACGGGAGGCAGCAG |
| 27 | 907R | CCGTCAATTCMTTTRAGTTT |
| 28 | 341F | CCTACGGGAGGCAGCAG |
| 29 | 907R | CCGTCAATTCMTTTRAGTTT |
| 30 | 189F | GGNGACTGGGACTTCTGG |
| 31 | 661R | CCATTYCTGCAACGMGGCC |
| 32 | 189F | GGNGACTGGGACTTCTGG |
| 33 | 682R | CGSAAGAAGAGNCGSAAG |
| 34 | CYA106F | CGGACGGGTGAGTAACGCGTGA |
| 35 | 104F | GGCGVACGGGTGAGTAA |
| 36 | 530R | CCGCNGCNGCTGGCAC |
| 37 | 357F | CCTACGGGAGGCAGCAG |
| 38 | 926R | CCGTCAATTCMTTTRAGT |
| 39 | Alf28fe | ARCGAACGCTGGCGGCA |
| 40 | Alf684re | TACGAATTTYACCTCTACA |
| 41 | Beta359f | GGGGAATTTTGGACAATGGG |
| 42 | Beta682r | ACGCATTTCACTGCTACACG |
| 43 | Gamma395f | CMATGCCGCGTGTGTGAA |
| 44 | Gamma871r | ACTCCCCAGGCGGTCDACTTA |
| 45 | CFB555f | CCGGAWTYATTGGGTTTAAAGGG |
| 46 | CFB968r | GGTAAGGTTCCTCGCGTA |
| 47 | CYA361f | GGAATTTTCCGCAATGGG |
| 48 | CYA785r | GACTACWGGGGTATCTAATCC |
| 49 | Plancto352fe | GGCTGCAGTCGAGRATCT |
| 50 | Plancto920re | TGTGTGAGCCCCCGTCAA |
| 51 | Firm350fe | GGCAGCAGTRGGGAATCTTC |
| 52 | Firm814re | ACACYTAGYACTCATCGTTT |
| 53 | 9bfm | GAGTTTGATYHTGGCTCAG |

TABLE 1-continued

The following Primers may be used with the methods of the present invention

| SEQ ID NO.: | primer | Sequence |
|---|---|---|
| 54 | 1512uR | ACGGHTACCTTGTTACGACTT |
| 55 | 8F | AGAGTTTGATCCTGGCTCAG |
| 56 | 27F | AGAGTTTGATCMTGGCTCAG |
| 57 | CYA106F | CGGACGGGTGAGTAACGCGTGA |
| 58 | CC [F] | CCAGACTCCTACGGGAGGCAGC |
| 59 | 357F | CTCCTACGGGAGGCAGCAG |
| 60 | CYA359F | GGGGAATYTTCCGCAATGGG |
| 61 | 515F | GTGCCAGCMGCCGCGGTAA |
| 62 | 533F | GTGCCAGCAGCCGCGGTAA |
| 63 | 895F | CRCCTGGGGAGTRCRG |
| 64 | 16S.1100.F16 | CAACGAGCGCAACCCT |
| 65 | 1237F | GGGCTACACACGYGCWAC |
| 66 | 519R | GWATTACCGCGGCKGCTG |
| 67 | CYA781R | GACTACWGGGGTATCTAATCCCWTT |
| 68 | CD [R] | CTTGTGCGGGCCCCCGTCAATTC |
| 69 | 902R | GTCAATTCITTTGAGTTTYARYC |
| 70 | 904R | CCCCGTCAATTCITTTGAGTTTYAR |
| 71 | 907R | CCGTCAATTCMTTTRAGTTT |
| 72 | 1100R | AGGGTTGCGCTCGTTG |
| 73 | 1185mR | GAYTTGACGTCATCCM |
| 74 | 1185aR | GAYTTGACGTCATCCA |
| 75 | 1381R | CGGTGTGTACAAGRCCYGRGA |
| 76 | 1381bR | CGGGCGGTGTGTACAAGRCCYGRGA |
| 77 | 1391R | GACGGGCGGTGTGTRCA |
| 78 | 1492R (1) | GGTTACCTTGTTACGACTT |
| 79 | bac339F | CTCCTACGGGAGGCAGCAG |
| 80 | bac815R | TTGTGCGGGCCCCCGTCAATT |
| 81 | bac907R | CCGTCAATTCMTTTRAGTTT |
| 82 | 341Fbac | CCTACGGGAGGCAGCAG |
| 83 | bac515F | GTGCCAGCMGCCGCGGTAA |
| 84 | bac806R | GGACTACVSGGGTATCTAAT |
| 85 | 530F | GTGCCAGCMGCNGCGG |
| 86 | 1100R | GGGTTNCGNTCGTTR |
| 87 | bac799F | ACCMGGATTAGATACCCKG |
| 88 | bac1394R | ACGGGCGGTGTGTRC |
| 89 | 926F | AAACTYAAAKGAATTGACGG |
| 90 | bac1394R | ACGGGCGGTGTGTRC |

TABLE 1-continued

The following Primers may be used with the methods of the present invention

| SEQ ID NO.: | primer | Sequence |
|---|---|---|
| 91 | 939F | TTGACGGGGGCCCGCAC |
| 92 | 1492r | TACCTTGTTACGACTT |
| 93 | bac1100F | YAACGAGCGCAACCC |
| 94 | bac1492R | GGGTTACCTTGTTACGACTT |
| 95 | bac317R | AAGGAGGTGATCCAGCC |
| 96 | bac1114F | GCAACGAGCGCAACCC |
| 97 | BaciMAJF | AGATTGCCCAGGCCTCTCG |
| 98 | BaciMAJR | CCATCGTAGTCTTAACCATAAAC |
| 99 | chloroF | TGGCCTATCTTGTTGGTCTGT |
| 100 | ChloroR | GAATCAACCTGACAAGGCAAC |
| 101 | Leg225 | AAGATTAGCCTGCGTCCGAT |
| 102 | Leg858 | GTCAACTTATCGCGTTTGCT |
| 103 | FAFfungiF1 | TCYSGCATCGATGAAGAACG |
| 104 | FAFfungiR1 | GATATGCTTAAGTTCAGCGGG |
| 105 | SSUfungiF | TGGAGGGCAAGTCTGGTG |
| 106 | SSUFungiR | TCGGCATAGTTTATGGTTAAG |
| 107 | ENDOITSF | AAGGTCTCCGTAGGTGAAC |
| 108 | ENDOITSR | GTATCCCTACCTGATCCGAG |
| 109 | ITS1Fgood | TCCGTAGGTGAACCTGCGG |
| 110 | ITS4R | TCCTCCGCTTATTGATATGC |
| 111 | ITS1Fgood | TCCGTAGGTGAACCTGCGG |
| 112 | ITS4R | TCCTCCGCTTATTGATATGC |
| 113 | rumFunF | TCCTACCCTTTGTGAATTTG |
| 114 | rumFunR | CTGCGTTCTTCATCGTTGCG |
| 115 | ITS1F | CTTGGTCATTTAGAGGAAGTAA |
| 116 | ITS4R | TCCTCCGCTTATTGATATGC |
| 117 | Euk7F | AACCTGGTTGATCCTGCCAGT |
| 118 | Euk570R | GCTATTGGAGCTGGAATTAC |
| 119 | Euk528F | CCGCGGTAATTCCAGCTC |
| 120 | EukR18R | cgttatcggaattaaccagac |
| 121 | euk1391F | GTACACACCGCCCGTC |
| 122 | EukB-Rev | TGATCCTTCTGCAGGTTCACCTAC |
| 123 | Euk516F: | GGAGGGCAAGTCTGGT |
| 124 | Euk1055R: | CGGCCATGCACCACC |
| 125 | arc340F | CCCTAYGGGGYGCASCAG |
| 126 | arc1000R | GAGARGWRGTGCATGGCC |
| 127 | arch915R | GTGCTCCCCCGCCAATTCCT |

TABLE 1-continued

The following Primers may be used with the methods of the present invention

| SEQ ID NO.: | primer | Sequence |
|---|---|---|
| 128 | archea349F | GYGCASCAGKCGMGAAW |
| 129 | archaea806R | GGACTACVSGGGTATCTAAT |
| 130 | arch344F | ACGGGGYGCAGCAGGCGCGA |
| 131 | arch915R | GTGCTCCCCCGCCAATTCCT |
| 132 | arch774R | CCCGGGTATCTAATCC |
| 133 | forwardMYCO | tgggaaactgggaaactgggtctaata |
| 134 | revMYCO | cccgcacgcccaagttaagctgtgag |
| 135 | mxaF1003F | GCGGCACCAACTGGGGCTGGT |
| 136 | mxaF1555R | CATGAABGGCTCCCARTCCAT |
| 137 | NS31 | TTGGAGGGCAAGTCTGGTGCC |
| 138 | AMLgood2 | GAACCCAAACACTTTGGTTTCC |
| 139 | mm01F | TAYATGTCNGGYGGTGTHGG |
| 140 | mm02R | ACRTTCATNGCRTAGTTNGG |
| 141 | nosZF | CGYTGTTCMTCGACAGCCAG |
| 142 | nosZR | CGSACCTTSTTGCCRTYGCG |
| 143 | Arch-amoAF | STAATGGTCTGGCTTAGACG |
| 144 | Arch-amoAR | GCGGCCATCCATCTGTATGT |
| 145 | bacamoA1F | GGGGTTTCTACTGGTGGT |
| 146 | bacamoA2R | CCCCTCKGSAAAGCCTTCTTC |
| 147 | Arch-amoAF | STAATGGTCTGGCTTAGACG |
| 148 | Arch-amoAR | GCGGCCATCCATCTGTATGT |
| 149 | 341-GC-F | CGCCCGCGCCGCCCCGCGCCCGTCCCGCCGCCCCCG CCCGCCTACGGGAGGCAGCAG |
| 150 | 907R | CCGTCAATTCMTTTRAGTTT |
| 151 | 341F | CCTACGGGAGGCAGCAG |
| 152 | 907R | CCGTCAATTCMTTTRAGTTT |
| 153 | 189F | GGNGACTGGGACTTCTGG |
| 154 | 661R | CCATTYCTGCAACGMGGCC |
| 155 | 189F | GGNGACTGGGACTTCTGG |
| 156 | 682R | CGSAAGAAGAGNCGSAAG |
| 157 | bacamoA1F | GGGGTTTCTACTGGTGGT |
| 158 | bacamoA2R | CCCCTCKGSAAAGCCTTCTTC |
| 159 | Arch-amoAF | STAATGGTCTGGCTTAGACG |
| 160 | Arch-amoAR | GCGGCCATCCATCTGTATGT |
| 161 | pmoA189F | GGNGACTGGGACTTCTGG |
| 162 | pmoA682R | CGSAAGAAGAGNCGSAAG |
| 163 | pmoA661R | CCATTYCTGCAACGMGGCC |
| 164 | gltA781F | ggggaccagctcatggtgg |

TABLE 1-continued

The following Primers may be used with the methods of the present invention

| SEQ ID NO.: | primer | Sequence |
|---|---|---|
| 165 | gltA1137R | aatgcaaaaagaacagtaaaca |
| 166 | nirSF | GTGAACGTCAAGGAAACGGG |
| 167 | nirSR | GAATTCGGATGCGTCTTGA |
| 168 | mcrF | GTCGGWTTCACMCAGTACGC |
| 169 | mcrR | TGCCCTCGTCKGACTGGTA |
| 170 | dsrF | CAACATCGTYCATACMCAGGG |
| 171 | dsrR | GTGTAGCAGTTACCGCA |
| 172 | nodCFI2F | CCGGATAGGMTGGKBCCRTA |
| 173 | nodCRI2R | GTGCACAASGCRTADRCCTTCAH |
| 174 | nirK1F | GGMATGGTKCCSTGGCA |
| 175 | nirK5R | GCCTCGATCAGRTTRTGG |
| 176 | W02 | GNTACCTTGTTACGACTT |
| 177 | R1492 | CTTAATTTGACTCAACACGG |
| 178 | corona1F | TCACANTTNGGATANTCCCA |
| 179 | corona1R | ACTCANNTNAATNTNAAATANGC |
| 180 | GLOM1310 | AGCTAGGYCTAACATTGTTA |
| 181 | GLOM5.8R | TCCGTTGTTGAAAGTGATC |
| 182 | LETC1670 | GATCGGCGATCGGTGAGT |
| 183 | ACAU1660 | TGAGACTCTCGGATCGG |
| 184 | GIGA5.8R | ACTGACCCTCAAGCAKGTG |
| 185 | ARCH1311 | TGCTAAATAGCCAGGCTGY |
| 186 | ITS-1F | CTTGGTCATTTAGAGGAAGTAA |
| 187 | ITS4i | TTGATATGCTTAAGTTCAGCG |
| 188 | S-C-Act-235-a-5-20 | CGCGGCCTATCATCAGCTTGTTG |
| 189 | S-C-Act-878-a-A-19 | CCGTACTCCCCAGGCGGGG |
| 190 | Acan1F | GGCCCAGATCGTTTACCGTGAA |
| 191 | Acan2R | TCTCACAAGCTGCTAGGGAGTCA |
| 192 | Euk18S300f | AGGGTTCGATTCCGGAG |
| 193 | EUK18S555R | GCTGCTGGCACCAGACT |
| 194 | prot1TitF | AACGGCTACCACATCTAAGGAACC |
| 195 | Prot1TitR | TTAAATACGAATGCCCCCAACTGT |
| 196 | diphyloF | GTGTTTCNNTGCGTGAGCCTGTTT |
| 197 | diphyloR | GTGGTAANCCGCACACACCAAANT |
| 198 | trypanosomeF | AATCGGCACAGTTTGATGAGCTG |
| 199 | trypanosomeR | CGTGGAGCGTGCGGTTTAATTTG |
| 200 | echinococcusF | CTGCTGCTGCTGCTACTACTGTA |

TABLE 1-continued

The following Primers may be used with the methods of the present invention

| SEQ ID NO.: | primer | Sequence |
|---|---|---|
| 201 | echinococcusR | TCCAGACGTCTTATGCCTTGCAC |
| 202 | taeniaF | TCCTTCATTGTTGTTGAGCCGAG |
| 203 | taeniaR | CAACATCGCCACGTGTAGCACA |
| 204 | trichurusF | AGGTCGTTGAAGAACGACGTGA |
| 205 | trichursR | TGGCAAAGACCATTGTGTGCAA |
| 206 | urcinariaF | AATTGTGGCAGCGGCAGATGTA |
| 207 | urcinariaR | TAGTTCACCATCTTTCGGGTCG |
| 208 | strongyloidesF | ACCATGGTTGTGACGGATAACG |
| 209 | strongyloidesR | TGGCAAATGCTTTCGCAGTAGG |
| 210 | cryptoF | ATGGCCGTTCTTAGTTGGTGGA |
| 211 | CryptoR | TGTGTACAAAGGGCAGGGACG |
| 212 | sarcocystisF | TGTCTAAGTGCGGCTGTCATAG |
| 213 | sarcocystisR | TAGTGCTGCTCACCACCATCCT |
| 214 | GenProtF | TGGAGCCTGCGGCTTAATTTGA |
| 215 | GenProtR | TGTGTACAAAGGGCAGGGACG |
| 216 | cycloIsoSarcoF | TGATGCCCTTAGATGTTCTGGG |
| 217 | cycloIsoSarcoR | TGTGTACAAAGGGCAGGGACG |
| 218 | entaGen1 | AAAGGAATTGACGGAAGGGCA |
| 219 | entaGen1R | AGCCCAAGATGTCTAAGGGCA |
| 220 | entaGen2F | TAGTGGTGCATGGCCGTTCTTA |
| 221 | entagen2R | TGTGTACAAAGGGCAGGGACG |
| 222 | ascarisF | ACGCAAAGTTGGCGACGACTA |
| 223 | ascarisR | CGGCTTAAACGAACTTGTGCA |
| 224 | hepatozoonF | ATGGTATTGGCTTACCGTGGC |
| 225 | hepatozoonR | CACCAGACTTGCCCTCCAATT |
| 226 | coxF | TTGTCGGTCGCCAGCAGATAC |
| 227 | coxR | CGGTGAACGGCGGGATGAACT |
| 228 | NL1F | GCATATCAATAAGCGGAGGAAA |
| 229 | NL4R | GGTCCGTGTTTCAAGACGG |
| 230 | adeno1F1 | ACTCCCATGAAACCATGCTACG |
| 231 | adeno1F2 | ACATACTTTGACATTCGCGGCG |
| 232 | adeno1R1 | ATACCGCCAAGTGGGAAGCAG |
| 233 | adeno1R2 | TCCGTAGCATGGTTTCATGGGA |
| 234 | adeno2F1 | TCCTGTGAGTGGGAACAAACCG |
| 235 | adeno2F2 | TCTCAGTGGAACGAAGCTGATG |
| 236 | adeno2R1 | TTGCCGGTCGTTCAAAGAGGTA |
| 237 | adeno2R2 | CACCCATGTTGCCAGTGCTGTT |

TABLE 1-continued

The following Primers may be used with the methods of the present invention

| SEQ ID NO.: | primer | Sequence |
|---|---|---|
| 238 | adeno3F1 | CATGCTGCGCAACGATACCAAT |
| 239 | adeno3F2 | TGGCATCGAGGATGAACTGCCT |
| 240 | adeno3R1 | TCATCAACCACCTGCCTGCTCA |
| 241 | adeno3R2 | CATTGCGGTGGTGGTTGAATGG |
| 242 | adeno5F1 | TAAGGGTTGACGGAGCCAGCAT |
| 243 | adeno5R1 | AGCCCTGGTAGCCAATGTTGTA |
| 244 | hMPVF1 | TGCACTATCACCTCTCGGTGCT |
| 245 | hMPVF2 | AGAAATGGGTCCTGAATCTGGG |
| 246 | hMPVR1 | AAACCGCCGTTGGTAACACCAT |
| 247 | hMPVR2 | AGCAGTGTAGATGATCGTGCAG |
| 248 | infApo1F1 | ACCACAGGNGTNGAGAAGCCT |
| 249 | infApo1F2 | TGCAGCCATGGATGACTTNCAN |
| 250 | infApo1R1 | TGAGAAAGCTTGCCCTCAATGC |
| 251 | infApo1R2 | ACACTTTCCCNATNGAGCCTTC |
| 252 | infBF1 | GGAAGGAATGATTGCAGGTTGG |
| 253 | infBR1 | GGTCTGGTTGCACTTGTGTTTGG |
| 254 | pinfluenza1F1 | TCAGTTATGCTCCTTGCCCACTG |
| 255 | pinfluenza1F2 | TCCTTGCCCACTGTGAATGAGAC |
| 256 | pinfluenza1R1 | TCCTATTTGCAGGTTGGAGTGCC |
| 257 | pinfluenza1R2 | TCCTATTTGCAGGTTGGAGTGCC |
| 258 | pinfluenza3F1 | AATCTGCAACACAACTGGGTGTC |
| 259 | pinfluenza3R1 | ACAATGCTCCCTGTGGGATTGAG |
| 260 | pinfluenzatype2F1 | AGCATCTGCGGAGAATGTGAAGG |
| 261 | pinfluenzatype2F2 | ATACTGGGAGCATGTCCAACACC |
| 262 | parainfluenzatype2R1 | AAGCTGTGATTCTGTGGTTGCTG |
| 263 | parainfluenzatype2R2 | TGGCCCATTGCCCTGTTGTATTT |
| 264 | LG12 | TAYMGNTAYGYNGAYTGG |
| 265 | LGR | ATNGGRTANACNCCCCA |
| 266 | nifHF | AAA GGY GGW ATC GGY AAR TCC ACC AC |
| 267 | nifHR | ATG ATG GCS ATG TAY GCS GCS AAC AA |
| 268 | nifHRb | TGS GCY TTG TCY TCR CGG ATB GGC AT |
| 269 | nifHRc | TGG GCY TTG TTY TCR CGG ATY GGC AT |
| 270 | nosZFb | AAC GCC TAY ACS ACS CTG TTC |
| 271 | nosZRb | TCC ATG TGC AGN GCR TGG CAG AA |
| 272 | nirK1F | Must use with nirS, functionally equivalent genes |
| 273 | nirK5R | |

TABLE 1-continued

The following Primers may be used with the methods of the present invention

| SEQ ID NO.: | primer | Sequence |
|---|---|---|
| 274 | nirS1F | Must use with nirK, functionally equivalent genes |
| 275 | nirS6R | |
| 276 | narG1960f | TAYGTSGGSCARGARAA |
| 277 | narG2650r | TTYTCRTACCABGTBGC |
| 278 | amoA1F | GGGGTTTCTACTGGTGGT |
| 279 | amoA2R | CCCCTCKGSAAAGCCTTCTTC |
| 280 | gagF | GATGACAGCATGTCAGGGAG |
| 281 | gagR | GTTGACAGGTGTAGGTCCTAC |
| 282 | rtxAl2 | GCAAGCGGGTGACAATGGCTTTAT |
| 283 | rtxA603 | GACAACGAGCTTTGCTTCATCGCA |
| 284 | PolyNF | NNNNNNNNNNNN |
| 285 | PolyNF | NNNNNNNNNNNNNNNNNN |

Due to advances in genetic sequencing approaches non-optical sequencing methods reduce the cost of molecular technology, genomics, and metagenomics, evaluating the genetics of microorganisms of all forms, including bacteria, fungi, helminths, protozoa, and viruses can be detected and identified based upon specific, universal or semi-universal (conserved and semi-conserved or specific) genes or transcripts. Novel methods have been developed and disclosed herein to improve diagnostics and empower the goals of subject-specific treatments into modern day practice.

Shotgun sequencing of RNA and DNA. DNA or RNA is extracted from a given human, animal or other environmental sample. This DNA is prepared using method to generate a sequencing library that is then sequenced using non-optical genetic sequencing apparati and method to evaluate the metagenome or consortium of genetic information from the given sample. This provides information on the identity of microorganisms, their antimicrobial resistance potential as well as their virulence factors.

Types of primers. Universal, specific, semi-universal, targeting kingdoms, super-kingdoms, targeting phylums, targeting all classes, families, orders, genus or species of microorganisms.

Barcodes: Types of barcodes are selected oligonucleotides that may be from 2 nucleotides to 200 nucleotides in length (preferably from 4 nucleotides to 10 nucleotides in length) and are used to identify, barcode, or define which sequences are derived from which specimen so that many specimens can be combined together in a non-optical genetic sequencing reaction and afterwards deconvoluted to resolve which genetic information resolves or relates to which sample.

Database formation: a nucleotide or protein database containing genetic information from all known microorganisms, formatted or raw to promote comparison of sequencing data to known or existing data for use in identifying microorganisms, characterizing microbial populations.

Methods are provided for performing DNA extraction from a wide range of specimen, then performing of microbial non-optical barcoded amplicon genetic sequencing that can detect and identify, through computational or bioinformatics methods, the profile of microorganisms within the specimen, the genes associated with antimicrobial resistance, the genes associated with virulence or pathogenicity. The method further, utilizes a database of known sequence information to compare against sequence information derived from the specimen to identify which microorganisms are present in the specimen. This in turn is followed by subsequent computational or bioinformatics algorithms which draws from a database containing information on antibiotic susceptibility, resistance information and previous treatment outcomes to obtain a profile of those antibiotics or therapeutics, which may be utilized to treat or positively impact the microbial profile identified. The computational system then generates interpretive diagnostic, virulence, antimicrobial resistance, and microbial ecology reports that elucidate the microbial assemblage and characteristics contained within the specimen and provide the associated therapeutic, treatment, remediation, or optimization options.

In broad terms, a preferred embodiment of the diagnostic, microorganism community assessment or microbial ecology method is the employment of non-optical sequencing processes (all previous patents dealing with genetic evaluation or sequence information have all been based upon optical sequencing methods by contrast), to identify microorganisms that may or may not be specifically targeted by assay thereby providing novel universal diagnostic methods based upon novel NON-optical genetic sequencing processes, this genetic sequencing using non-optical machines and processes for determining the microbial composition of any given sample is then followed by a computational system to characterize the microbial and genetic resistance profiles, virulence factors, and genetic information relevant to the health of a given sample source including animals, humans, and environmental sources, then computation methods are utilized to evaluate the genetic non-optical sequencing data and provide reports and interpretations.

An advantage of some embodiments is that it provides a cost effective molecular diagnostic method and microbial ecology characterization method. This improves the ability of clinicians, bioremediation specialists to evaluate, remediate, treat, monitor infections including polymicrobial and biofilm phenotype infections, microbial populations involved in industrial processes, microbial populations causing improvement or decay of industrial processes (such as oil well or water well fouling), veterinary infections, animal health enhancement such as feedlot productivity related to improving the microbial populations in an animals gastrointestinal tract thereby improving the utilization of feed (feed efficiency and conversion in animals), the use of probiotics and prebiotics to improve health and the associated monitoring of the microbial populations, bacterial infections not conducive to diagnosis by traditional culture based methodology. Another advantage is the ability to utilize the microbial profiles to determine which antibiotics may be utilized to most efficiently and effectively control or treat an infection, remediate an industrial process, enhance animal health, improve the efficiency of an industrial process related to microbial processes and assemblages and to do this evaluation diagnostic and monitoring of the microorganism populations using non-optical sequencing methods which are lower in cost than optical sequencing methods and to provide microbial ecology and infection monitoring in a comprehensive, less expensive and more rapid manner. Another advantage is that non-optical sequencing by being less expensive can generate more data and provide a more comprehensive evaluation of microbial assemblages allowing computational methods to provide a diagnostic, monitoring and therapeutic indication and interpretive report that can be utilized by a clinicians, industrial scientists, environmental microbiologist, and other individuals needing to optimize, diagnose treat, remediation, improve microbial processes, to easily evaluate and personalize approaches for improving or optimizing or changing or medially treating their subject, bioreactor, environment, animal in a personalized specific and targeted manner. Another advantage is that this method does not rely on the ability of a microorganism to be grown in the laboratory. Another advantage is that hard to culture, fastidious organism, organisms in biofilm phenotype and viable but non-culturable organism can be identified and all organisms can be quantified or relatively quantified. Another advantage is that patient-specific therapeutic regimes can be identified for clinicians to address the complex nature of polymicrobial or poor culturing microbial infections. Another advantage is that an algorithm for identifying such therapeutics, which can best target a specific microbial polymicrobial infection, can be determined.

Disclosed herein are methods for identifying and determining the amount of two or more pathogens in an individual subject or specimen using non-optical sequencing methods and equipment and processes, including asymptomatic subjects and subjects who are immunocompromised and asymptomatic with respect to the pathogenic disease(s) of interest, in order to monitor or diagnose or develop information relative to disease emergence and/or disease progression, and to evaluate the microbial diversity and evaluate the microbial ecology of any specimen where there are microorganisms present.

In one aspect, the methods disclosed herein permit identifying the presence and/or the relative or the specific quantity of two or more microorganisms, particularly bacterial, fungal, helminthal, protozoan or viral pathogens that may be present in any given environmental or biological specimen. The methods perform such utility through the using of non-optical genetic (DNA or RNA) sequencing methods of directly extracted RNA or DNA from the environmental or biological specimen.

The methods permit the detection and quantification of pathogens or microorganism via non-optical genetic sequencing of all available or specific polynucleotides, e.g., DNAs or RNAs isolated from an environmental, biological, or clinical specimen, both within a panel of reactions, in a multiplex format and in a highly parallelized sequencing pyrosequencing or future non-optical sequencing format, that can further permit the determination of levels (e.g., ratios, percentages, and quantities) for two or more target polynucleotides in a single reaction. Identification and quantification of pathogen specific targets in a specimen has a myriad clinical and microbial ecology utilities specifically to identification of differences between environments, to identify microorganisms and guide treatment, remediation, therapy, enhancement, optimization or other method of changing or monitoring the microorganisms from any given sample.

In one aspect, the methods described herein use shotgun approaches to generate sequence data for all aspects of the genetic makeup of the microoganisms in any sample or by using non-optical sequencing approaches to evaluate generated Polymerase chain reaction amplification products of known sizes that both differ from each other at the sequence level in specific regions of the polynucleotide and are the same or similar or conserved (same) in specific regions of the polynucleotide. Further, a set of oligonucleotide primers that are specific and target a DNA or RNA molecule isolated from the specimen that can be used to identify a given species, strain, genus, family, class, phylum, or order of microorganism by targeting non-conserved or conserved regions of a gene or part of the genetic material of the organism or a combination of the two.

In one aspect, the methods described herein relate to methods of estimating or determining the identification and/or quantification of microorganisms in a specimen following isolation (e.g., extraction or purification) of polynucleotides from the specimen, the method comprising: for a given pathogen specific target polynucleotide, selecting a pair of amplification primers that will generate a target amplicon of known length upon amplification of the target, e.g., by PCR or RT-PCR. The method will provide a relative or absolute quantification of the amount of the target, e.g., by spiking or applying known concentrations of a given template or the use of quantitative universal PCR approaches or other format of polymerase chain reaction.

In one aspect, methods described herein relate to the detection of selected pathogens in pre-symptomatic immunocompromised subjects. Since development of clinical symptoms can be subclinical in many infections and in immunocompromised subjects, particularly transplant recipients undergoing immunosuppressant therapy, quantitative rapid and or comprehensive detection of viral, bacterial and protozoan pathogens provides a means to guide therapy during the early stages of infection.

In one aspect, the methods analyze a specimen suspected of containing any of a polymicrobial community of predetermined or unknown pathogens by screening a specimen for a known and unknown pathogens specific, universal, semi-universal or conserved targets to be used in a nucleic acid amplification reaction to produce an amplicon from each pathogen specific target. The methods include selecting a series of pathogen-specific or kingdom based universal or semi-universal primer pairs wherein each primer pair corresponds to and is targeted to polynucleotide sequences specific to a corresponding pathogen or conserved or universal for all known or unknown microorganisms. The series of pathogen-specific primers or universal or semi-universal domain, kingdom, phylum, class, family, genus or species specific primers when used together produce amplicons of distinct sizes such that the presence of a specific or group of known or unknown pathogen in the specimen. Amplicons are detected by resolving a portion of the amplification mixture to determine if amplicons are present, and is so, their size and then amount of amplicon. Portions of the specimen may be sampled at intermediate points during amplification to determine when amplicons are first detectable, or at the end of amplification. Portions of the specimen may be sampled for downstream non-optical genetic sequencing.

In one aspect, the methods for quantifying a plurality of predetermined pathogens in a specimen suspected of containing at least one pathogen using non-optical genetic sequencing methods. The methods include obtaining a specimen suspected of containing at least one of the predetermined pathogens. The specimen may be obtained from the environment (e.g., soil, water, animal or human waste), from a plant, animal, frozen tissue banks, or human source (e.g., a pathogen carrier or host). Polynucleotides are isolated from the specimen for use as target in an amplification reaction to produce template. Pathogen-specific or universal or semi-universal primers are selected to correspond to each or all of the plurality of pathogens that could be present in the specimen. Control polynucleotides, preferably competitor polynucleotides, may also be included in the amplification reaction. The competitor polynucleotides can be templates for amplification by pathogen-specific primers, but produce amplicons of a distinct size from the products amplified from the specifically targeted or universal or semi-universal oligonucleotide primers using the same or any other pathogen-specific universal or semi-universal oligonucleotide primers with specimen-derived or control templates. Competitor polynucleotides are added at multiple specific but differing concentrations (i.e., copy numbers) to allow for determination or estimation of the quantity (i.e., copy number) of a pathogen-specific, universal or semi-universal nucleic acid amplifications generated from the specimen.

In one aspect, the methods include monitoring of a series of specimens from the same source for any of a predetermined plurality or multiplicity of pathogens. The methods include obtaining a specimen from a source at regular intervals (e.g., about continually, hourly, daily, weekly, about monthly, about quarterly or yearly) and quantifying the amount or relative amount of the composition of pathogen or multiple pathogens or specific or unknown organisms in the specimen using any amplification method and also followed by non-optical genetic sequencing methods. A source may be any specimen suspected clinically of containing microorganisms. By evaluating the microbial composition and relative or absolute abundance of pathogens at discrete, random or regular intervals, pathogens may be detected in the asymptomatic individual and appropriate measures can be taken, such as modification of administration of compositions that result in immunosuppression of the individual or administration of a therapy to ameliorate and/or treat the pathogen infection.

The present invention relates generally to an approach that utilize non-optical methods and universal gene targets (targets that are universal among all microorganisms such as the 16s gene for Achaea and bacteria and the 18s gene for fungi, and the ITS gene for fungi) for detecting the presence of and determining the identity of microorganisms thereby decreasing the cost of the technology and thereby increasing its utility for a variety of purposes. The present invention is directed to the resolution of the complete microbial community of etiologic agents and commensal flora present in samples including, but not limited to, animals, humans, environmental, clinical, or other samples, including samples of unknown origin from which knowledge of the complete microbial community is of scientific and/or medical interest. The invention is further directed to the determination of detailed genetic information about the individual organisms which are detected and identified that make up in the sample's microbiome including identification of genes that predict or indicate sensitivity or susceptibility of the organism to antimicrobials, antibiotics, or other chemical compounds, ions, or elements.

DNA or RNA is extracted from specimen(s).

A universal primer such as the universal 16s universal ribosomal primers that pick up a broad range of analytes (e.g., bacteria or archaea) or targets and sample or specimen specific barcodes are used to detect any and all a universal tag are utilized to amplify and or label a set of analytes from a specimen(s) to provide a diagnostic or analysis of monitoring method.

A secondary labeling step or direct labeling will incorporate a sample specific tag/label/barcode that are specific to a sample. This allows many samples to be analyzed through non-optical molecular genetic sequencing approaches.

All previously existing methods for sequencing and performing the above processes use or incorporate an optical sequencing step.

The sample can then be analyzed using a biochemical method (such as generation of hydrogen ions) to generate a signal that is then detected using a semi-conductor chip that can act as a highly multiplex pH meter.

Both highly specific assays for detecting individual analytes for diagnostic purposes and the very broad range or universal diagnostic assays based upon previous optical sequencing technologies have limitations. Primarily there is a much higher cost to the use of optical sequencing due to the need of high powered optics such as CCD cameras, the expense of generating visual signals during sequencing such as the use of fluorescence (light generating reagents and chemicals). Specific assays are limited in that the user must know what analyte is being targeted, if not, the user is limited to analyte detection or targeting by trial and error. Universal or highly broad range methods pick up all the analytes within a group and therefore unknown targets or analytes are missed. The primary issue solved by this invention is that previous sequencing technologies, which were based upon optical sequencing (e.g. pyrosequencing) utilized for universal bacterial detection, are based upon expensive optical sequencing technologies.

The method described herein uses universal or broad range primers and individual sample specific barcodes or tags (as have been well described in the literature), in order to analyzed batches or multiple specific specimens or subjects or sample detecting many specific targets that are grouped together to create a single assay. This assay will be analyzed using a cost effective pH sensor, wave-guide, semi-conductor technology or other non-optical method for determining the sequence of molecular material such as nucleic acids (RNA or DNA). One example is to sequence each of the multiplexed analytes based upon pH generation detected using technology exemplified by a semi-conductor or other silicon or wave guide chip-based technology. The present invention allows many analytes to be screened all at once using broad range (e.g. kingdom specific, genus specific, family or class or sub-groups of organisms or targets) to be screened all at once and allows many different samples to be analyzed all together.

Common diagnostic methods involving genetic or molecular determination of the code of a molecule, i.e., sequencing using a florescence detected by a camera or laser and/or other optical method for measurement. The present invention avoids the problems associated with optical sequencing techniques and uses a combination of non-optical sequencing and universal gene targets (targets that are universal among all microorganisms such as the 16s gene for archaea and bacteria and the 18s gene for fungi, and the ITS gene for fungi) for detection and determining the identity of microorganisms thereby decreasing the cost of the technology and thereby increasing its utility for a variety of purposes.

Other inventions or processes utilizing optical methods require more specialized and more expensive chemicals and reagents. Optical methods increase the cost of the diagnostic methods.

Because this invention does not utilize optical methods (such as laser or CCD camera, etc.) and instead measures a chemical change or property (e.g. pH change or increase in molecular weight) then the cost of the technology is reduced dramatically thereby improving the feasibility of the diagnostic applications.

DNA or RNA is extracted using a method to generate purified RNA or DNA, which can be mechanical or enzymatic. Purification generally includes removing some, any or all non-analyte material through selective enrichment of analytes/target or depleting inhibitors.

A set of universal or highly comprehensive (e.g. for bacteria the 16s gene can be universal for all bacteria, for fungi the ITS1-4 region is highly comprehensive) amplifying primers are used. Thus, a 16s and ITS assay can be combined. One or more very broad range or universal or comprehensive primers (non-specific primers) targeting a variety of similarly related analytes (e.g. targeting all bacteria, or targeting a class of viruses, or targeting a class of molecules or a family of genes, or a kingdom of organisms, etc.) are mixed with the sample along with other buffers and biochemical reagents. Next, an enzymatic method such as the PCR or linear amplification is then utilized to join together the primers and the analytes. Then, the sample is analyzed using a non-optical molecular sequencing methodology. The data generated by the previous step is analyzed using computational approaches to provide a diagnosis.

In one example of the present example, RNA and or DNA is extracted (e.g., step 1) from receipt of sample but may be extracted at any time up to the analysis (step #3) from a sample using a chemical or physical method that generates a template. This template contains zero or up to 1 million or more analytes that will be detected directly or after processing through steps 2-3. These analytes may be directly measured without steps 2-3, or steps 2 and 3 may occur together. Step 4 can be integrated with step 3. Together the steps may be used separately or together and in any order within the process.

A number of universal or broad range primers that is between 1 and 1 million broad range primers (universal primers e.g. two primers that can amplify by means of the PCR 20% of all bacteria or 80% of all bacteria or 100% of all bacteria or between 20% and 100% of all bacteria). Bacteria in this instance represent one of many targets that may be analytes for diagnostic, monitoring, or research purposes. Samples can then be batched together or may be mixed together with the sample during DNA and or RNA extraction. Each of the specific primers will be targeted for a group of analytes (e.g. all HLA genes), primers A universal for target group A, primers B universal for target group B, . . . Primers N (where N is any number between 3 and 1 million or more) specific for target group N, are utilized to mix with the DNA or RNA from the specimen(s), and then create a Step 3 ligation or an amplification with the purpose of generating directly or indirectly each detectable group specific analyte between 0 and 1 million or more for each specimen. Step 3 can be performed within an enzymatic step or process such as the polymerase chain reaction or directly through a linear amplification process or through other general mechanisms of amplification.

DNA and RNA are extracted using one of many common methods from physical and chemical disruption. Many DNA and RNA extraction kits are sold commercially and methods for DNA extraction are well known.

Primers are designed to detect groups of targets of known analytes at the kingdom or phylum level (highly universal or comprehensive). These analytes can be, but are not limited to, microorganisms such as the phylum spirochetes or the kingdom bacteria, or the kingdom fungi, e.g., 1 primer set rather than 3000 primer sets. Many samples can be analyzed in multiplex as each individual sample will have a unique barcode/tag or primer. These primers are then mixed in equimolar ratios and utilized to amplify or enrich the targets from the DNA and RNA extracted in step 1. On each primer we have a 4-25 bp or larger sample specific barcode. This same barcode is utilized for all samples. Thus, we have a design 5' XX-PrimerAF and 5' YYYYYYYYYY-primerAR. Where XXXXXXXXX represents the forward common label and YYYYYYYYY represents the reverse common label. The primerAF represents the forward primer targeting analyte A, and primer AR represents the reverse primer targeting analyte A. This continues such that for sample N we would have XXXXXXXXX-PrimerNF and YYYYYYYYYYYYYY-primerNR. This common tag can be used for all the analytes because it is the same. Thus, we have a highly multiplex reaction that amplifies the targets allowing them to be enriched. We can then use a secondary labeling approach to add on unique and sample specific barcodes resulting in the following after rounds of ligation, linear amplification or PCR/PCR-like amplification.

BarcodeA-XXXXXXXXX-BroadRangePrimerF—Analyte N's SPECIFIC REGION—BroadRangePrimerR-YYYYYYYYYY-BarcodeA . . . which would be specific for sampleA and which would amplify a broad range of analytes within the N family or class or genus or kingdom or phyla or other broad category of analyte similar but within sample.

BarcodeB-XXXXXXXXXX-PrimerNF—Analyte N's SPECIFIC REGION—PrimerNR-YYYYYYYYYY-BarcodeB . . . which would be specific for sampleB and analyte N groups within Sample B; where barcodes A, B, C, D, etc., are examples of unique barcodes that delineate a specific sample that is then utilized by software downstream to deconvolute information and data and diagnosis when run in a highly multiplexed assay format and where Primers are broad range designed to cover large populations of analytes. Examples include but are not limited to different classes of genes e.g. 16s ribosomal gene, 23s ribosomal, functional genes such as nirS, etc.

With this sample labeling system we can multiplex many different samples and many different analytes and the resulting multiplexed data can be resolved back to the sample and to the analyte.

The present invention can also be used with semi-conductor technology. One example of which is the ion torrent technology or the IBM semi-conductor genetic sequencing technology. The key feature and difference in this is the use of non-optical sequencing technologies. This is in contrast to optical sequencing methods. Non-optical sequencing uses a sensor that measures changes in the molecular state of the molecule (in this example DNA) such that as bases are added there is a change in the pH of the environment which can be measured, e.g., through use of a semi-conductor chip. This is in contrast to optical methods that produce fluorescence when sequencing or light, which are measured by laser or CCD camera respectively (i.e. measured using optical methods). The highly multiplexed sample is then prepared to create an appropriate library that can be placed within the semi-conductor technology and analytes without fluorescence or other optical technologies.

Following the analysis using non-optical sequencing technologies, bioinformatics and software tools are utilized to analyze the data and provide reports as the presence of the analytes, concentration, mutations within the analytes, species, genus of the analytes, thereby providing a diagnostic tool that can be used by scientists and physicians.

DNA and RNA are extracted using one of many common methods from physical and chemical disruption. Many DNA and RNA extraction kits are sold commercially and methods for DNA extraction are well known.

Primers are designed to specifically target broad ranges of analytes. These analytes can be pathogens such as all bacteria or all fungi or all protozoa or comprehensive groups of microorganisms such as all spirochetes. In this example if the user wishes to target all the known spirochetes, and there are 3000 known spirochetes, primers are designed (1 primer pair for instance) that will detect all spirochetes. Thus, if there are many different samples, the user could label each of these samples with a unique barcode but use the sample primer pair and many samples at the same time could be evaluated for spirochetes (in this example). These primers from each sample are mixed in equimolar ratios and utilized to amplify or enrich the targets from the DNA and RNA extracted in step 1. On each primer there is a 4-25 bp or larger unique barcode utilized for each unique sample. 100 samples=100 unique barcodes. As such, the design can be: 5'XXXXXXXXX-PrimerAF and 5' YYYYYYYYYY-primerAR, where XXXXXXXXX represents the unique barcode label and YYYYYYYYY represents the reverse unique barcode label. The forward label and the reverse label can be the same or different. The primerAF represents the forward primer targeting a group of analytes represented by A and primer AR represents the reverse primer targeting analyte group A. This continues such that for sample N we would have XXXXXXXXN-PrimerAF and YYYYYYYYYYN-primerAR. Thus, the unique barcode, label, or tag to be used for each sample is different but we can have a different tag on the forward and reverse primer. Thus, a highly multiplexed reaction that amplifies the targets allows them to be enriched where many samples can be analyzed at the same time. The labeling can be done as one reaction or as multiple reactions to incorporate the barcode, tag etc., e.g., with a single PCR we incorporate the barcode and sequencing primers. The user can then use a secondary labeling approach to add on unique and sample specific barcodes resulting in the following after rounds of ligation, linear amplification or PCR like amplification.

BarcodeA-XXXXXXXXXX-PrimerNF—Analyte N's SPECIFIC REGION—PrimerNR-YYYYYYYYYY-BarcodeA . . . which would be specific for sampleA and the analyte N within sample.

BarcodeB-XXXXXXXXXX-PrimerNF— Analyte N's SPECIFIC REGION—PrimerNR-YYYYYYYYYY-BarcodeB . . . which would be specific for sampleB and analyte N withing Sample B, where barcodes A, B, C, D etc are specific to a sample and where Primer A, B C, D etc., are specific to an analyte.

With this dual labeling system the user can multiplex many different samples and many different analytes and the resulting multiplexed data can be resolved back to the sample and to the analyte.

Non-optical sequencing technology, such as semi-conductor sensor technology, can then be used to sequence the analyte that have been amplified using very small sample sizes. One example of a non-optical method for sequencing is the Life Technologies "ion torrent" technology or the IBM semi-conductor genetic sequencing technology.

The highly multiplexed sample is then prepared to create an appropriate library that can be placed within the semi-conductor technology and analyzed without fluorescence or other labeling technologies that rely on optical technologies such as cameras or lasers. Following the analysis, bioinformatics and software tools are used to analyze the data and provide reports as the presence of the analytes, concentration, mutations within the analytes, species, genus of the analytes, thereby providing a diagnostic tool that can be used by scientists and physicians.

Adding specific technologies to increase the ability to generate longer sequences or to improve the mixing together in equimolar ratios the individual samples and analytes from each sample. Technologies to enhance the ability to process more samples and more analytes, as well as, methods to lower the cost of doing the multiplex initial labeling reactions can also be incorporated into the present invention. As noted it may not be necessary to amplify the analytes if they can be pulled out through an enrichment technique such as magnetic bead hybridization and target enrichment protocols. In this method, biotin or other labels on probes specific to the analytes can also be used. The user can extract enough DNA to allow for a rapid ligation step that incorporates our barcodes for the samples. The user can then use computation approaches to deconvolute and identify the analytes and which samples they were derived from.

A much lower cost method that involves using highly multiplexed reactions with many different specific targets for many specific analytes. Thus, if the user wishes to detect all respiratory pathogens primers specific to each of the respiratory pathogen are used. After the steps listed above, the user can determine that sample A from patient A was positive for pathogen B. The user can also find that sample B from patient B was positive for pathogen HH. Therefore, the user can now have a diagnosis for both patients.

In addition to the realm of diagnostic testing, the invention can be used for research purposes. There are many forms of non-optical sequencing technologies such as sequencing using semi-conductor chips, which can measure pH changes and many methods for incorporating both the analyte specific primers with their common code and the sample specific codes. Many sequencing methods that do not rely on optical methods may be utilized. Many different types of computational algorithms can be utilized to take the data from the sequencing device and analyze it in a variety of ways to generate a report to give to the scientist or physician. Many computer languages can be used to design software to analyze and generate reports.

Data form analysis may identify new types of pathogens that cause disease and may help to identify new treatments for existing pathogens. The technology can be used as a monitoring technology in addition to a diagnostic technology. The technology and process can be used to identify mutations among hundreds of different genes as part of genetic screening in humans and animals. The technology can be used for parentage testing, for studies on phylogeny and systematics, and the technology and process can be used to identify polymicrobial disease contributors, e.g., may be used to target the top 1000 bacteria associated with skin infections. Thus, the user would utilize 1 primer set targeting a broad range of bacteria known to reside in skin infections. This technology differs from prior art due to the use of a combination of primers and non-optical sequencing technologies as a process for diagnostics and research use.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Stager C E, Davis J: Automated systems for identification of microorganisms. Clinical microbiology reviews 1992, 5(3):302-327.
2. York M, Brooks G, Fiss E: Evaluation of the autoSCAN-W/A rapid system for identification and susceptibility testing of gram-negative fermentative bacilli. Journal of clinical microbiology 1992, 30(11):2903-2910.
3. Stark R P, Maki D G: Bacteriuria in the catheterized patient. New England Journal of Medicine 1984, 311(9): 560-564.
4. Koenig C, Tick L, Hanna B A: Analyses of the FlashTrack DNA probe and UTIscreen bioluminescence tests for bacteriuria. Journal of clinical microbiology 1992, 30(2): 342-345.
5. Pezzlo M T, Amsterdam D, Anhalt J P, Lawrence T, Stratton N J, Vetter E A, Peterson E M, de la Maza L M: Detection of bacteriuria and pyuria by URISCREEN a rapid enzymatic screening test. Journal of clinical microbiology 1992, 30(3):680-684.
6. Persing D H: Diagnostic molecular microbiology: principles and applications: ASM Press; 1993.
7. Bergeron M, Quellette M: Diagnosing bacterial infectious diseases in one hour: an essential upcoming revolution. Infection 1995, 23(2):69-72.
8. Martineau F, Picard F J, Roy P H, Ouellette M, Bergeron M G: Species-specific and ubiquitous-DNA-based assays for rapid identification of *Staphylococcus aureus*. Journal of Clinical Microbiology 1998, 36(3):618-623.
9. Ehrlich G D, Greenberg S J: PCR-based diagnostics in infectious disease. 1994.

10. Tang Y, Persing D: Molecular detection and identification of microorganisms. Manual of clinical microbiology, 7th ed American Society for Microbiology, Washington, D.C. 1999:215-244.
11. Weaver G, Krause J, Miller T, Wolin M: Incidence of methanogenic bacteria in a sigmoidoscopy population: an association of methanogenic bacteria and diverticulosis. Gut 1986, 27(6):698-704.
12. Reeve J N: Archaebacteria then . . . Archaes now (are there really no archaeal pathogens?). Journal of bacteriology 1999, 181(12):3613-3617.
13. Belay N, Johnson R, Rajagopal B, de Macario E C, Daniels L: Methanogenic bacteria from human dental plaque. Applied and environmental microbiology 1988, 54(2):600-603.
14. Belay N, Mukhopadhyay B, De Macario E C, Galask R, Daniels L: Methanogenic bacteria in human vaginal samples. Journal of clinical microbiology 1990, 28(7):1666-1668.
15. Relman D A, Persing D H, Persing D: Genotypic methods for microbial identification. PCR protocols for emerging infectious diseases: a supplement to Diagnostic Molecular Microbiology: Principles and Applications ASM Press, Washington, D.C. 1996:3-31.
16. Persing D H: PCR protocols for emerging infectious diseases: a supplement to Diagnostic Molecular Microbiology: principles and applications: Amer Society for Microbiology; 1996.
17. Chen K, Neimark H, Rumore P, Steinman C R: Broad range DNA probes for detecting and amplifying eubacterial nucleic acids. FEMS microbiology letters 1989, 57(1):19-24.
18. McCabe K M, Zhang Y H, Huang B L, Wagar E A, McCabe E R B: Bacterial species identification after DNA amplification with a universal primer pair. Molecular genetics and metabolism 1999, 66(3):205-211.
19. Van Burik J A, Myerson D, Schreckhise R W, Bowden R A: Panfungal PCR assay for detection of fungal infection in human blood specimens. Journal of Clinical Microbiology 1998, 36(5):1169-1175.
20. Fox G E, Wisotzkey J D, Jurtshuk P: How close is close: 16S rRNA sequence identity may not be sufficient to guarantee species identity. International Journal of Systematic Bacteriology 1992, 42(1):166-170.
21. Clayton R A, Sutton G, Hinkle Jr P S, Bult C, Fields C: Intraspecific variation in small-subunit rRNA sequences in GenBank: why single sequences may not adequately represent prokaryotic taxa. International journal of systematic bacteriology 1995, 45(3):595-599.
22. Sanger F, Nicklen S, Coulson A R: DNA sequencing with chain-terminating inhibitors. Proceedings of the National Academy of Sciences 1977, 74(12):5463.
23. Ewing B, Hillier L D, Wendl M C, Green P: Base-calling of automated sequencer traces usingPhred. I. Accuracy assessment. Genome research 1998, 8(3):175-185.
24. Metzker M L: Sequencing technologies—the next generation. Nature Reviews Genetics 2009, 11(1):31-46.
25. Ansorge W J: Next-generation DNA sequencing techniques. New biotechnology 2009, 25(4):195-203.
26. Maxam A M, Gilbert W: A new method for sequencing DNA. Proceedings of the National Academy of Sciences 1977, 74(2):560.
27. Nyrén P, Lundin A: Enzymatic method for continuous monitoring of inorganic pyrophosphate synthesis. Analytical biochemistry 1985, 151(2):504-509.
28. Ronaghi M: Pyrosequencing sheds light on DNA sequencing. Genome research 2001, 11(1):3-11.
29. Hyman E D: A new method of sequencing DNA. Analytical biochemistry 1988, 174(2):423-436.
30. Ronaghi M, Uhlén M, Nyrén P: A sequencing method based on real-time pyrophosphate. Science 1998, 281 (5375):363-365.
31. Ronaghi M, Karamohamed S, Pettersson B, Uhlén M, Nyrén P: Real-time DNA sequencing using detection of pyrophosphate release. Analytical biochemistry 1996, 242 (1):84-89.
32. Schuster S C: Next-generation sequencing transforms today's biology. Nature 2008, 200(8).
33. Aebersold R, Mann M: Mass spectrometry-based proteomics. Nature 2003, 422(6928):198-207.
34. Theuwissen A J P: CMOS image sensors: State-of-the-art. Solid-State Electronics 2008, 52(9):1401-1406.
35. Rothberg J M, Hinz W, Rearick T M, Schultz J, Mileski W, Davey M, Leamon J H, Johnson K, Milgrew M J, Edwards M: An integrated semiconductor device enabling non-optical genome sequencing. Nature 2011, 475(7356): 348-352.
36. Purushothaman S, Toumazou C, Ou C P: Protons and single nucleotide polymorphism detection: A simple use for the ion sensitive field effect transistor. Sensors and Actuators B: Chemical 2006, 114(2):964-968.
37. Pourmand N, Karhanek M, Persson H H J, Webb C D, Lee T H, Zahradniková A, Davis R W: Direct electrical detection of DNA synthesis. Proceedings of the National Academy of Sciences 2006, 103(17):6466-6470.
38. Milgrew M, Riehle M, Cumming D: A large transistor-based sensor array chip for direct extracellular imaging. Sensors and Actuators B: Chemical 2005, 111:347-353.
39. Milgrew M J, Cumming D R S: Matching the transconductance characteristics of CMOS ISFET arrays by removing trapped charge. Electron Devices, IEEE Transactions on 2008, 55(4):1074-1079.
40. Hammond P, Cumming D: Encapsulation of a liquid-sensing microchip using SU-8 photoresist. Microelectronic engineering 2004, 73:893-897.

What is claimed is:

1. A method for determining the identity of one or more microorganisms in a sample comprising the steps of:
   (a) isolating DNA or RNA from the sample;
   (b) combining the DNA or RNA directly with one or more universal amplification primers, wherein the one or more universal amplification primers are specific for one or more microorganisms;
   (c) amplifying the DNA, or the RNA following reverse transcription with a reverse transcriptase, wherein the universal amplification primers for the step of amplifying the DNA, or the RNA following reverse transcription with a reverse transcriptase, are SEQ ID NOS: 83 and 84, and further comprising amplifying with one or more primers specific for at least one of 23s ribosomal nucleic acids, nirS, rpoB, COX1, rbcL, LSU, 28S, fusA, ileS, lepA, leuS, pyrG, recA, recG, rplB, or SSU;

(d) contacting the amplification products of step (c) with one or more microorganism-specific detectable markers, wherein each detectable marker is a non-optical detectable marker;

(e) detecting the amplification products of step (c) with a non-optical detector; and (f) determining both the presence or absence of the microorganism in the sample, and a copy number of the microorganism when the microorganism of the one or more target microorganisms is present.

2. The method of claim 1, wherein the microorganism-specific detectable marker is selected from a tag, label, or barcode.

3. The method of claim 1, wherein the amplification products of step (c) is further characterized with a non-optical nucleic acid sequencer.

4. The method of claim 1, wherein the microorganism is defined further as a fungi and, the amplification products of step (c) is further amplified with with one or more primers specific for 18S ribosomal nucleic acids.

5. The method of claim 1, wherein the microorganism is defined further as a fungi and further comprising amplifying the DNA or RNA of the sample with one or more primers are specific for internal transcribed spacer (ITS) nucleic acids.

6. The method of claim 1, wherein the amplification of step (c) comprises PCR or linear amplification of the DNA or RNA followed by non-optical sequencing of amplicons of the amplified DNA or RNA to identify microorganisms.

7. The method of claim 1, further comprising amplifying the DNA or RNA of the sample with one or more primers selected for a single specific species, wherein amplification and detection of a product is species specific.

8. The method of claim 1, wherein further comprising the steps of detecting and identifying known or suspected microorganisms using non-optical sequencing.

9. The method of claim 1, further comprising the step of using non-optical sequencing to identify a specific microorganism in the sample and determining an amount of specific microorganism polynucleotides in the sample.

10. The method of claim 1, further comprising the step of using non-optical sequencing to diagnose an environmental, industrial, veterinary, or medical sample for microorganisms.

11. The method of claim 1, further comprising the step of using non-optical sequencing to characterize the microbiological composition of an environmental, industrial, veterinary, or medical sample.

12. The method of claim 1, further comprising the step of using non-optical sequencing to determine the relative percentage of microorganisms in an environmental, industrial, veterinary, or medical sample.

13. The method of claim 1, further comprising the step of generating a report using non-optical sequencing to determine the relative percentage of microorganisms in an environmental, industrial, veterinary, or medical sample and based on those finding selecting at least one of a treatment, a therapy, an improvement, or a remediation.

14. A method for determining the identity of one or more microorganisms in a sample comprising the steps of:
(a) isolating DNA or RNA from the sample;
(b) combining the DNA or RNA with one or more universal amplification primers, wherein the one or more primers are specific for one or more microorganisms;
(c) amplifying the DNA, or the RNA following reverse transcription with a reverse transcriptase, wherein the primers for the step of amplifying the DNA, or the RNA following reverse transcription with a reverse transcriptase, are SEQ ID NOS: 83 and 84, and further comprising amplifying with one or more primers specific for at least one of 23s ribosomal nucleic acids, nirS, rpoB, COX1, rbcL, LSU, 28S, fusA, ileS, lepA, leuS, pyrG, recA, recG, rplB, or SSU;
(d) detecting the amplification products of step (c) with a non-optical detector; and
(e) determining the identity of the microorganism with a non-optical nucleic acid sequencer.

15. The method of claim 14, further comprising the step of contacting the amplification product of step (c) with a microorganism-specific detectable marker selected from a tag, label, or barcode.

16. The method of claim 14, wherein the microorganism is defined further as a fungi and further comprising amplifying the DNA or RNA of the sample with one or more primers specific for 18S ribosomal nucleic acids.

17. The method of claim 14, wherein the microorganism is defined further as a fungi and further comprising amplifying the DNA or RNA of the sample with one or more primers specific for internal transcribed spacer (ITS) nucleic acids.

18. The method of claim 14, wherein the amplification of step (c) comprises PCR or linear amplification.

19. The method of claim 14, further comprising amplifying the DNA or RNA of the sample with one or more primers selected for a single specific species, wherein amplification and detection of any product is species specific.

20. The method of claim 14, further comprising the steps of detecting and identifying the microorganisms using non-optical sequencing.

21. The method of claim 14, further comprising the steps of detecting and identifying known or suspected microorganisms using non-optical sequencing.

22. The method of claim 14, wherein the non-optical sequencer is used to identify and quantitate microorganisms.

23. The method of claim 14, wherein the non-optical sequencer is used to diagnose an environmental, industrial, veterinary, or medical sample for microorganisms.

24. The method of claim 14, wherein the non-optical sequencer is used to characterize the microbiological composition of an environmental, industrial, veterinary, or medical sample.

25. The method of claim 14, further comprising the step of determining the relative percentage of microorganisms in an environmental, industrial, veterinary, or medical sample.

26. The method of claim 14, further comprising the step of generating a report using non-optical sequencing to determine the relative percentage of microorganisms in an environmental, industrial, veterinary, or medical sample and based on those finding selecting at least one of a treatment, a therapy, an improvement, or a remediation.

* * * * *